US011996007B2

(12) United States Patent
Foley et al.

(10) Patent No.: US 11,996,007 B2
(45) Date of Patent: May 28, 2024

(54) TRAINING DEVICE

(71) Applicant: SHORE PRODUCT GROUP LIMITED, Edinburgh (GB)

(72) Inventors: Nicholas Foley, Edinburgh (GB); Gavin Fraser McDougall, Edinburgh (GB); James Donald McLusky, Edinburgh (GB); William Jeremy Davies, Edinburgh (GB)

(73) Assignee: SHORE PRODUCT GROUP LIMITED, Edinburgh (GB)

( * ) Notice: Subject to any disclaimer, the term of this patent is extended or adjusted under 35 U.S.C. 154(b) by 1055 days.

(21) Appl. No.: 16/649,585

(22) PCT Filed: Sep. 21, 2018

(86) PCT No.: PCT/GB2018/052700
§ 371 (c)(1),
(2) Date: Mar. 20, 2020

(87) PCT Pub. No.: WO2019/058135
PCT Pub. Date: Mar. 28, 2019

(65) Prior Publication Data
US 2020/0258425 A1 Aug. 13, 2020

(30) Foreign Application Priority Data
Sep. 21, 2017 (GB) ..................... 1715237

(51) Int. Cl.
*G09B 23/28* (2006.01)
*A61M 5/20* (2006.01)
(Continued)

(52) U.S. Cl.
CPC ............. *G09B 23/285* (2013.01); *A61M 5/20* (2013.01); *A61M 5/31543* (2013.01);
(Continued)

(58) Field of Classification Search
CPC ....... G09B 23/28; G09B 23/285; G09B 23/30
See application file for complete search history.

(56) References Cited

U.S. PATENT DOCUMENTS 5,071,353 A * 12/1991 van der Wal ....... A61M 5/2033
434/262
7,682,155 B2 * 3/2010 Raven .................. G09B 23/285
434/262
(Continued)

FOREIGN PATENT DOCUMENTS

WO 2017044662 A1 3/2017
WO 2017060017 A1 4/2017
(Continued)

OTHER PUBLICATIONS

European Patent Office/ISA, International Search Report on Application No. PCT/GB2018/052700, dated Dec. 12, 2018.

*Primary Examiner* — Kurt Fernstrom
(74) *Attorney, Agent, or Firm* — PERKINS IP LAW GROUP LLC; Jefferson Perkins

(57) ABSTRACT

A training device (10) for training a user in the operation of an auto-injector that dispenses a medicament is described. The training device (10) comprises a housing (13), an actuation assembly (22) located within the housing (13), the actuation assembly (22) comprising a plunger (24) and a guide member (26), the plunger and the guide member defining, and connected by, a complementary first male profile and a first female profile. The plunger (24) is movable with respect to the guide member (26) along a first path defined by at least a portion of the first male or the first female profiles, the plunger (24) moving linearly between a start position and a finish position. The first path extends in a direction non-parallel to the linear movement of the plunger (24).

21 Claims, 23 Drawing Sheets

(51) Int. Cl.
*A61M 5/315* (2006.01)
*A61M 5/32* (2006.01)

(52) U.S. Cl.
CPC ..... *A61M 5/3202* (2013.01); *A61M 2005/208* (2013.01); *A61M 2205/581* (2013.01); *A61M 2205/582* (2013.01); *A61M 2205/583* (2013.01); *A61M 2205/587* (2013.01)

(56) References Cited

U.S. PATENT DOCUMENTS

| | | | |
|---|---|---|---|
| 8,398,593 | B2 | 3/2013 | Eich et al. |
| 8,714,984 | B2* | 5/2014 | Mach ................. A61M 5/20 |
| | | | 434/272 |
| 9,911,364 | B2 | 3/2018 | Baker et al. |
| 10,013,895 | B2* | 7/2018 | Swanson ............. G09B 23/285 |
| 10,089,902 | B2 | 10/2018 | Baker et al. |
| 10,235,905 | B2* | 3/2019 | Su ..................... G09B 23/285 |
| 10,255,827 | B2* | 4/2019 | Bendek .............. G09B 23/285 |
| 2012/0040320 | A1* | 2/2012 | Nadeau ............... G09B 23/285 |
| | | | 434/262 |
| 2013/0102971 | A1* | 4/2013 | Olson ................. A61M 5/2033 |
| | | | 604/198 |
| 2013/0266919 | A1* | 10/2013 | Baker .................. G09B 19/00 |
| | | | 434/262 |
| 2015/0235571 | A1* | 8/2015 | Alexandersson . A61M 5/31501 |
| | | | 434/262 |
| 2016/0193416 | A1 | 7/2016 | Olson et al. |
| 2018/0350265 | A1 | 12/2018 | Baker et al. |

FOREIGN PATENT DOCUMENTS

| | | |
|---|---|---|
| WO | 2017087570 A1 | 5/2017 |
| WO | 2017144211 A1 | 8/2017 |
| WO | 2017153077 A1 | 9/2017 |
| WO | 2018104011 | 6/2018 |
| WO | 2018183772 A2 | 10/2018 |
| WO | 2019006210 A1 | 1/2019 |
| WO | 2019023252 A1 | 1/2019 |

* cited by examiner

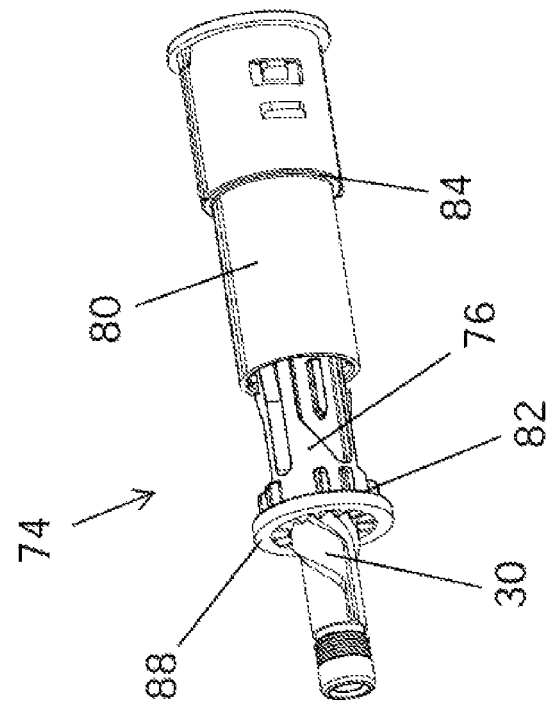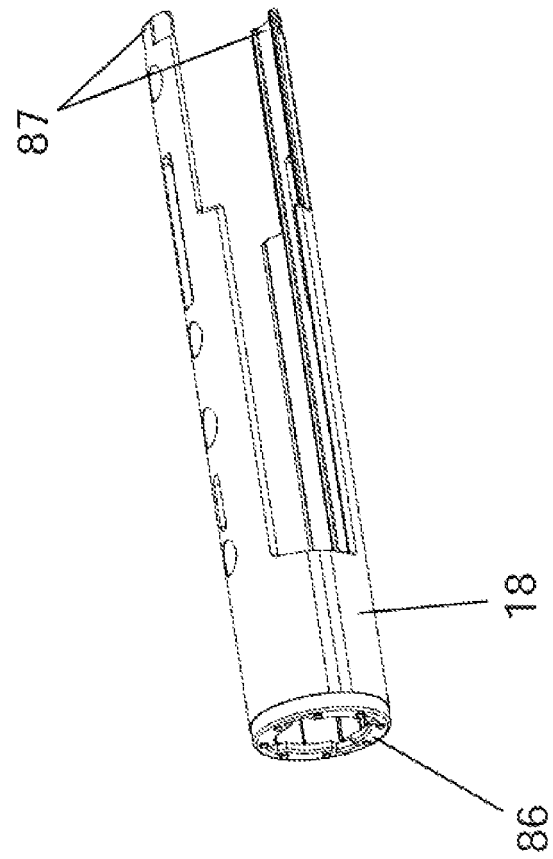
FIGURE 9

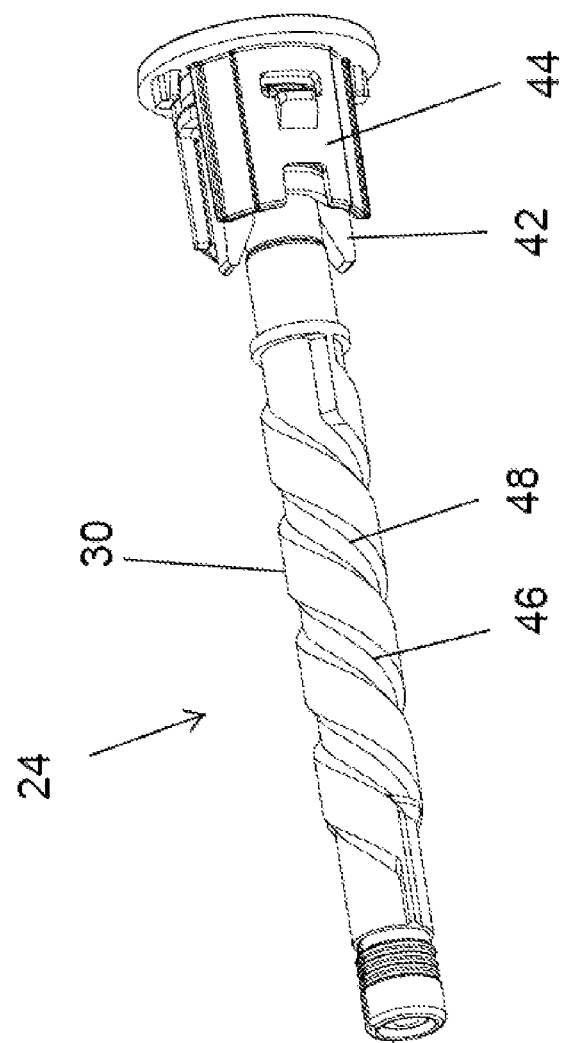
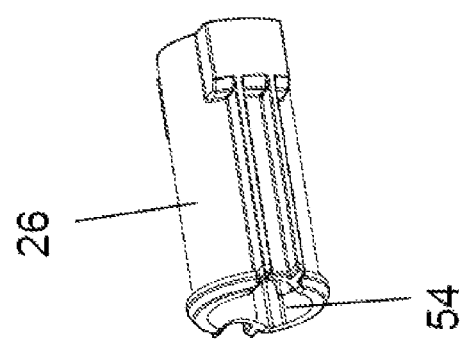
FIGURE 15

TRAINING DEVICE

FIELD

The present invention generally relates to an injector training device and, more particularly, to a training device for an auto-injector.

BACKGROUND

Automatic injectors are devices for enabling an individual to self-administer a dosage of a liquid medicament subcutaneously or intramuscularly.

A typical auto-injector has a housing, inside of which is a cartridge containing medicament. During use, a needle extends from the auto-injector into the user such that the medicament is subsequently forced through the needle and into the user. After delivery of the dose of medicament into the injection site, a needle shield may safely cover and shield the used needle tip from further use.

It is often important that the user of an auto-injector learn its proper operation and become comfortable with its use. Users should not hesitate to inject themselves, either from fear of using the device or for lack of knowledge in the proper use of the device, especially during a critical moment when an injection is required. However, it is impractical for individuals to train with automatic injectors by repeatedly injecting themselves.

Devices that simulate the operation of an auto-injector whereby the user can practice and become familiar with the auto-injector's operation prior to dispensing any medicament are known. Training with such a device may help to prevent improper administering of the medicament, improper orienting of the auto-injector, and premature removal of the auto-injector prior to the full dispensing of the medicament.

These training devices often have a plunger which travels down the training device to replicate the movement of a syringe plunger in an actual device. In an actual device the liquid medicament resists the movement of the plunger. To provide a realistic simulation, some training devices utilise a damping mechanism to replicate the resistance of a liquid medicament.

Conventional training devices however have drawbacks. It has been found in some devices that the damping mechanism, used to resist movement of the dispensing plunger, do not sufficiently dampen the plunger meaning that the time it takes the training device plunger to travel down training device is faster than the time it takes the plunger in a real device, resulting in an inaccurate simulation. Indeed, it has been found that in some conventional devices this inaccuracy is compounded by wear over time resulting in shorter and longer travel times.

SUMMARY

According to a first aspect of the present invention, there is provided a training device for training a user in the operation of an auto-injector that dispenses a medicament, the training device comprising:
 a housing;
 an actuation assembly located within the housing, the actuation assembly comprising a plunger and a guide member, the plunger and the guide member defining, and connected by, a complementary first male profile and a first female profile, the plunger being movable with respect to the guide member along a first path defined by at least a portion of the first male or the first female profiles, the plunger moving linearly between a start position and a finish position,
 wherein the first path extends in a direction non-parallel to the linear movement of the plunger.

In at least one embodiment of the present invention, a training device for training a user in the operation of an autoinjector that dispenses a medicament is provided in which a plunger moves along a first path in the form of, for example a helical groove defined by the plunger, the helical groove being part of a helical connection in which the guide member defines a protrusion which runs in the groove. The first path being non-parallel to the linear movement of the plunger means the path is of greater length than the linear distance the plunger travels when moving from the start position to the finish position. Such an arrangement means that the time the plunger takes to move from the start to the finish position can be controlled by the selection of, in this example, a longer or shorter helical pitch.

The linear movement of the plunger may be rectilinear. The rectilinear motion of the plunger may be in the direction defined by a longitudinal axis of the plunger.

In one embodiment, the guide member may be connected to an external surface of the plunger.

The guide member may encircle the plunger.

The guide member may define a throughbore, the plunger passing through the throughbore.

In an alternative embodiment, the plunger may define a bore, the guide member being connected to an internal surface of the plunger.

The guide member may be supported by a bracket within the housing. The bracket may be in a fixed position within the housing at least in normal use of the training device. The guide member may have no or substantially no freedom for motion in the direction of the linear movement of the plunger. The guide member may have limited freedom for motion in the direction of the linear movement of the plunger. The guide member may be held captive by the bracket with limited freedom for motion in the direction of the linear movement of the plunger.

The guide member may be held captive by a bracket with limited freedom for motion in the direction of the linear movement of the plunger and have freedom of motion to rotate about a plunger longitudinal axis. The rotation of a guide member in such an arrangement may be stopped when the plunger is moving from the start position to the finish position, for example by the guide member moving linearly into a locked relationship with the bracket. Contacting surfaces of the guide member and the bracket can be formed and arranged to be rotationally locked when pressed together (e.g. they have corresponding serrations). This rotational locking allows the plunger to move along the first path with the guide member fixed relative to the housing of the training device.

The guide member may be prevented from rotating about the plunger longitudinal axis, for example by a supporting bracket.

In a preferred embodiment, the first path may encircle a plunger longitudinal axis. In such an embodiment, the plunger rotates as it moves linearly between the first position and the second position.

In this embodiment, the path may be helical.

The complementary male and female profiles may define a threaded connection.

In an alternative embodiment, the path may be serpentine. The path may, in some cases, not encircle the plunger longitudinal axis. In such a case the plunger may, for example, rotate a partial turn clockwise followed by a partial turn anticlockwise.

There may be more than one path. For example, there may be two paths. Paths may start at opposite sides of the plunger the plunger longitudinal axis. Two paths on opposite sides of the plunger longitudinal axis can provide balanced support for the plunger as it travels between the start and finish positions.

The actuation assembly may further comprise a biasing mechanism. The biasing mechanism may be configured to bias the plunger towards the finish position. The use of a biasing mechanism means that the time the plunger takes to move from start to finish position can also be controlled by the selection of a stronger or weaker biasing mechanism.

The biasing mechanism may be an energy accumulating member.

The energy accumulating member may be a compression spring. A compression spring is a simple and effective way of biasing plunger towards the finish position.

The actuation assembly may further comprise a support member configured to support the plunger as it moves between the start position and the finish position.

The support member may be different to the guide member. In alternative embodiments, support member and the guide member are the same.

The plunger may be in a sliding relationship with the support member.

The plunger may be telescopically arranged with the support member.

The support member may be axially fixed with respect to the plunger.

The support member may be rotationally connected to the plunger.

The support member may be rotationally connected to the plunger by a key and key way relationship.

The actuation assembly may further comprise a damping mechanism. The damping mechanism may be provided to provide further control of the time the plunger takes to move from the start to the finish position.

The damper may be a rotary damper.

The support member may be connected to the rotary damper such that rotation of the support member is damped by the rotary damper. In an arrangement where the plunger and support member are rotationally connected, rotation of the plunger is damped through the support member by the rotary damper.

In alternative embodiments, the damper may be a linear damper or any suitable damping mechanism may be used.

The training device may further comprise a removable cap, the cap cooperating with the housing to provide a sealed unit.

Removal of the cap may reveal an open end defined by a cover sleeve, the cover sleeve configured to be the point of engagement with an injection site. By injection site it is meant the location at which the user is simulating injection of a medicament using the training device.

The training device may further comprise a trigger mechanism to trigger the actuation mechanism to start the movement of the plunger from the start position.

The trigger mechanism may trigger the actuation mechanism upon a user pressing the training device against a surface.

The training device cover sleeve may be configured to simulate a cover sleeve on an actual auto-injector. On an auto-injector, a cover sleeve is provided to prevent exposure of the needle outwith normal operation.

The cover sleeve may be movable with respect to the housing. The cover sleeve may act as an initiator, with movement of the cover sleeve, when pressed against an injection site, triggering the actuation mechanism.

In alternative embodiments, the trigger mechanism may be a button. The button may create a mechanical interaction which triggers the training device and/or recreate an electronic interaction to trigger the training device. The trigger mechanism may be an electronic trigger.

The training device may further comprise a locking mechanism. The locking mechanism may be configured to prevent further operation until the device is unlocked, for example by use of a release mechanism. The release mechanism may be configured to unlock the locking device and reset the device. Resetting the device may include returning the plunger to its start position and setting a trigger mechanism. The locking device may prevent further operation by being configured to prevent the plunger returning from the finish position to the start position.

The locking device may prevent further operation by being configured to prevent movement of a moveable cover sleeve, following a simulated injection. This simulates a real device where after one injection and removal of the device from the skin, the cover sleeve may re-extend to cover the needle and lock in position, to prevent accidental reuse or needle stick injury.

The training device may further comprise a release mechanism adapted to release the locking mechanism. For example, to allow the plunger to return to the start position from the finish position or to allow a cover sleeve to move again.

The release mechanism may be configured to engage the plunger.

The release mechanism may be configured to engage the guide member with a locking mechanism, engagement of the guide member with the locking mechanism releasing the locking mechanism.

The release mechanism may be part of the removable cap.

Replacement of the removable cap may release locking mechanism.

For example, replacement of the removable cap may release locking mechanism allowing the plunger to return to the start position from the finish position and/or allow a moveable cover sleeve to move again. Such arrangements mean the training device has to be returned to a prior to use state, that is with the housing sealed by the removable cap before it can be used. This accurately reflects the situation with a real autoinjector.

Various types of locking mechanism may be employed. Release may be by replacing the cap so that the cap or a release tool fitted to the cap can engage with the locking mechanism e.g. via the plunger and/or the guide member.

Conveniently the locking mechanism may constitute part of the trigger mechanism that releases the plunger of the actuation assembly, to allow it to travel from the start position towards the finish position. In embodiments of the training device the plunger is urged to move from the start position by a biasing member, such as a compression spring. This movement may be prevented by a latch, such as a retaining clip, of the trigger mechanism that engages the plunger. For example, the latch engages an end of the plunger distal to the end of the device including a moveable cover sleeve that acts as the point of engagement with an injection site. To mimic a real injection device, release of the latch (to allow the plunger to move) may be obtainable by pressing the moveable cover sleeve against an injection site so that the cover sleeve moves relative to the training device housing. Release of the latch may be by the cover sleeve acting directly on the latch to release the plunger. As a convenient alternative the cover sleeve may engage the locking mechanism, which in turn may act on the latch.

In some embodiments the locking mechanism may comprise a locking mechanism body in a sliding (telescopic) relationship with a corresponding locking mechanism housing such as a collar. The locking mechanism body is biased away from the locking mechanism housing by a biasing member such as a compression spring. The plunger of the training device passes through the locking mechanism body and (when in the start position) engages a latch of the trigger mechanism located within the locking mechanism housing. To release the plunger, the moveable cover sleeve is pressed against an injection site, causing its end distal to the injection site to push and move the locking mechanism body within the locking mechanism housing, engaging the latch to release the plunger. After the simulated injection is completed, (and pressure on the moveable cover sleeve released), the locking mechanism body is moved away from the locking mechanism housing by the action of its biasing member; and locks into position so that a repeated pressing of the cover sleeve against an injection site does not allow substantial movement of the cover sleeve.

Locking and unlocking the locking mechanism can be achieved in various ways with such embodiments. In some embodiments the guide member has a limited motion in the linear direction of the plunger, (i.e. generally in the axial direction of the trainer device). This motion is sufficient to enable the guide member to engage and disengage with components of the locking mechanism.

In some examples the locking mechanism body may be directed to rotate relative to the locking mechanism housing, when sliding telescopically towards the locking mechanism housing, so that on the return, as the body and housing move away from each other, a locking catch operates, preventing further telescopic movement until the mechanism is unlocked. The rotary motion may be provided by having one or more projections on the locking mechanism housing that engage one or more grooves of the locking mechanism body. The groove or grooves define a rotary track or tracks, forcing rotation when there is telescopic motion between the housing and the body. As an alternative the projection(s) may be on the locking mechanism body and the groove(s) on the locking mechanism housing. A locking catch may comprise a projection sliding in a groove that deflects a resilient locking arm as it passes, the arm then prevents return motion of the projection back along the track. The locking catch may be provided as part of a rotary track arrangement or may be provided separately between the locking mechanism body and corresponding locking mechanism housing. Release of such a locking catch may be by rotation of the projection out of alignment with the resilient locking arm. Conveniently this unlocking rotation may return the locking mechanism housing to a position where it is ready to act again as part of the trigger release mechanism.

This unlocking rotation may be achieved in various ways. In a convenient arrangement a guide member can be used to effect the desired unlocking rotation.

For example, a guide member that defines a through bore with the plunger passing through it is held captive in the housing of the training device by a bracket that supports it, with limited freedom for motion in the direction of the linear movement of the plunger. The plunger first path is helical in relation to the guide member. To return the plunger to the first position a setting tool, (e.g. provided on an end cap) is inserted into the housing to push the plunger linearly back towards its first position. As the plunger moves the guide member also moves, until it engages the locking mechanism body. The contacting surfaces of the guide member and locking mechanism body are formed and arranged to be rotationally locked when pressed together (e.g. they have corresponding serrations). Continued motion of the plunger towards its first position causes the guide member to rotate, (because of the helical path relationship between plunger and guide member). This rotation rotates the locking mechanism body back to its unlocked position at the same time as the plunger is moved back, ultimately to its first position, with the trigger mechanism reset.

In other examples a locking and unlocking arrangement that requires only linear motion of the locking mechanism body and the guide member may be employed.

As with the arrangements having rotational locking/unlocking discussed above, the locking mechanism may comprise a locking mechanism body in a sliding (telescopic) relationship with a corresponding locking mechanism housing such as a collar. The locking mechanism body is biased away from the locking mechanism housing by a biasing member such as a compression spring. The plunger of the training device passes through the locking mechanism body and (when in the start position) engages a latch of the trigger mechanism located within the locking mechanism housing.

In these embodiments the guide member is supported by a bracket and held captive with a limited amount of linear motion but no rotational motion permitted. The locking mechanism body includes one or more projections that are radially resiliently deformable in the radial direction. The guide member has one or more corresponding slots that accept the projections.

When the projections of the locking mechanism body are accepted into the slots of the guide member, they are moved radially inwards so that the projections on the locking mechanism body can slide telescopically into the locking mechanism housing. When the projections of the locking mechanism body are not accepted into the slots of the guide member, or constrained within the locking mechanism housing, they extend radially outwards of the diameter of the housing. In this position the projections lock the locking mechanism body, preventing its telescopic movement towards the locking mechanism housing.

When a training device of these embodiments is in the start position, the projections of the locking mechanism body are accepted into the slots of the guide member. To release the plunger, the moveable cover sleeve is pressed against an injection site, causing its end distal to the injection site to push and move the locking mechanism body, telescopically within the locking mechanism housing, engaging the latch to release the plunger.

As the locking mechanism body moves telescopically within the locking mechanism housing, the projections move out of the corresponding slots in the guide member but are constrained from radially outwards movement by the locking mechanism housing.

On release of the plunger the guide member is driven linearly towards the bracket, by the action of the plunger. Thus, the guide member is moved distally from the locking mechanism body to the extent allowed by the bracket.

After the simulated injection is completed, (and pressure on the moveable cover sleeve released), the locking mechanism body is moved away from the locking mechanism housing by the action of its biasing member. As the guide member has already been moved away from its start position the projections on the locking mechanism body move radially outwards as they exit the locking mechanism housing, blocking the body from returning into the housing.

Release of this lock may be obtained by returning the plunger to the first position with a setting tool (e.g. provided on an end cap). The setting tool is inserted into the housing to push the plunger linearly back towards its first position. When the plunger is nearly back in the first position it engages the guide member for linear motion, pushing the guide member until the slots accept the projections of the locking mechanism body, moving them radially inwards. Telescopic motion of the locking mechanism body into the locking mechanism housing is permitted again, as the projections can now slide into the locking mechanism housing.

The training device may further include at least one sensor adapted to provide feedback to user on the successful operation of the device.

The feedback may be visual such as a display or a flashing light.

The feedback may be audible such as a sequence of beeps or clicks.

The feedback may be haptic such as a vibration.

The training device may further include a mechanical feedback mechanism configured to provide feedback to user tactile feedback to user.

The training device may provide feedback through a third party application such as on a smart phone.

According to a second aspect of the present invention, there is provided a training device for training a user in the operation of an auto-injector that dispenses a medicament, the training device comprising:

a housing having a longitudinal axis;

an actuation assembly located within the housing, the actuation assembly comprising a plunger, the plunger being movable along the longitudinal axis between a start position and a finish position, a biasing member, the biasing member biasing plunger towards the finish position, and a damper, the damper configured to damp the movement of the plunger from the start position to the finish position, wherein the damper acts in a plane perpendicular to the longitudinal axis.

According to a third aspect of the present invention, there is provided an actuation assembly comprising a plunger and a guide member, the plunger and the guide member defining, and connected by, a complementary first male profile and a first female profile, the plunger being movable with respect to the guide member along a first path defined by at least a portion of the first male or the first female profiles, the plunger moving linearly between a start position and a finish position, wherein the first path extends in a direction non-parallel to the linear movement of the plunger.

According to a fourth aspect of the present invention, there is provided an actuation assembly comprising a plunger, the plunger being movable along the longitudinal axis between a start position and a finish position, a biasing member, the biasing member biasing plunger towards the finish position, and a damper, the damper configured to damp the movement of the plunger from the start position to the finish position, wherein the damper acts in a plane perpendicular to the longitudinal axis.

It will be understood that features described as being non-essential or preferable with respect to the first aspect may be equally applicable to the other aspects and have not been repeated for brevity.

BRIEF DESCRIPTION OF THE DRAWINGS

An embodiment of the present invention will now be described with reference to the accompanying drawings in which:

FIG. 9 is a partially exploded perspective view of part of the training device of FIG. 1 showing part of the locking mechanism;

FIG. 15 is an exploded view of the actuation assembly of the training device of FIG. 14;

DETAILED DESCRIPTION OF THE DRAWINGS

Figure 1:
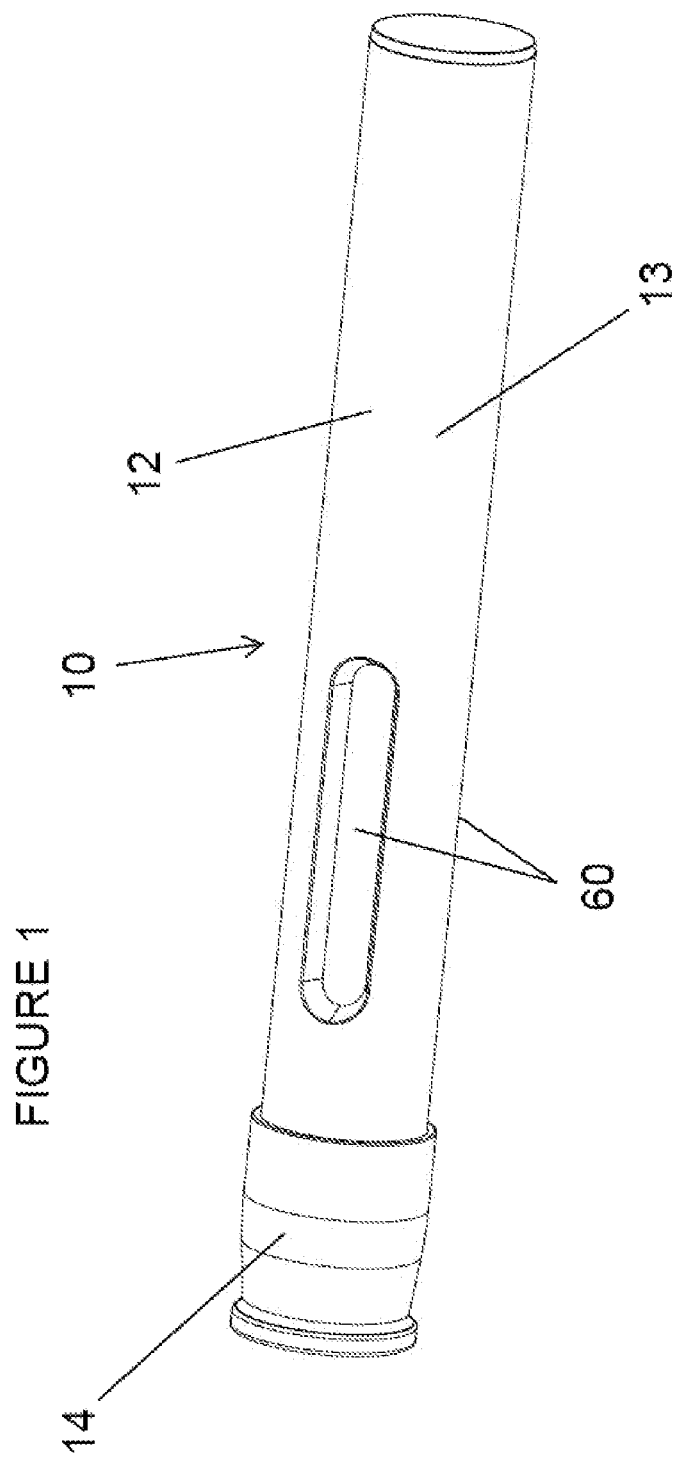
FIG. 1 is a perspective view of a training device, for training a user in the operation of an autoinjector that dispenses a medicament.
Figure 2:
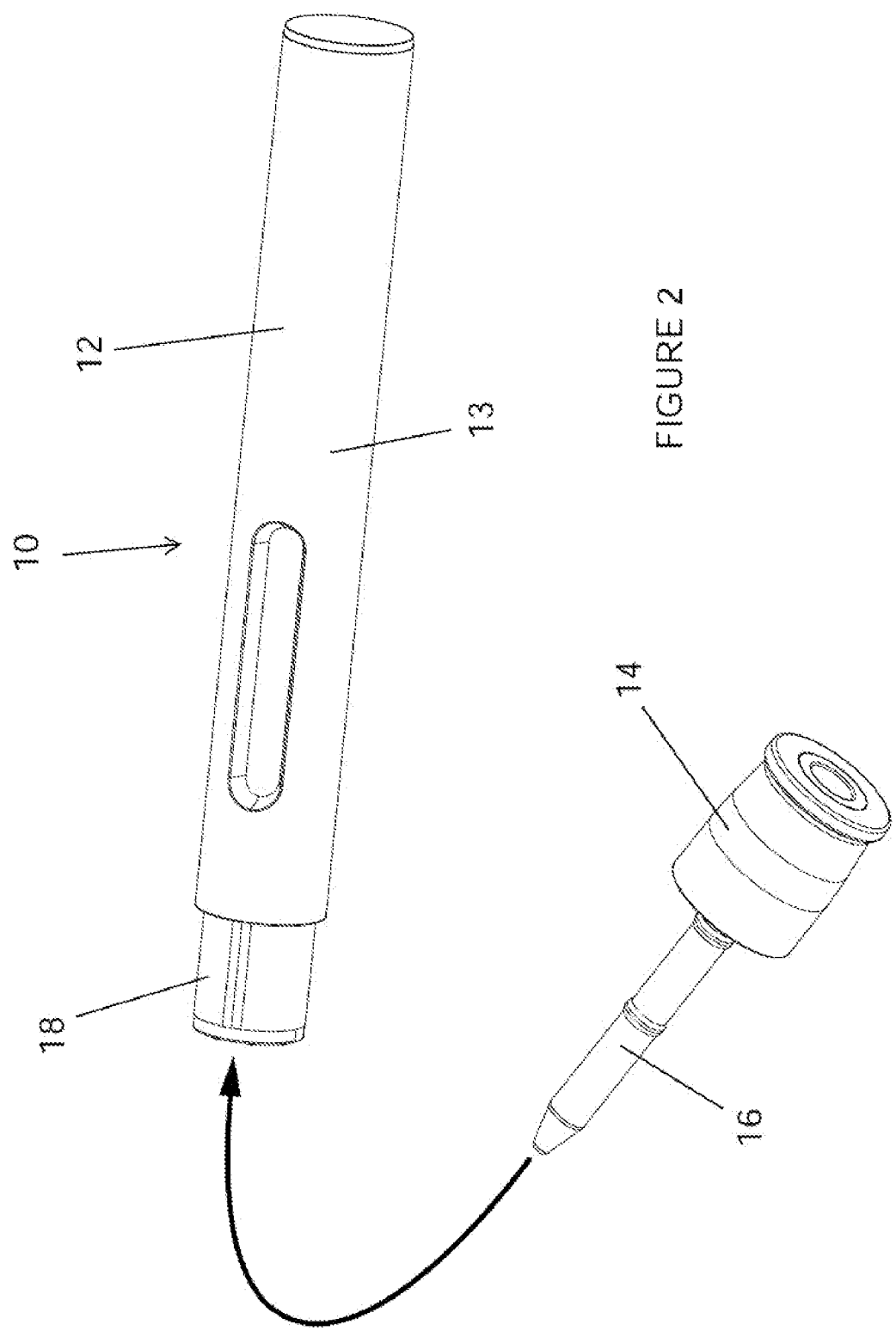
FIG. 2 is a partially exploded view of the training device of FIG. 1.

Reference is first made to FIG. 1, a perspective view of a training device, generally indicated by reference numeral 10, for training a user in the operation of an autoinjector that dispenses a medicament, and FIG. 2 a partially exploded view of the training device 10 of FIG. 1.

The training device 10 comprises a housing assembly 12 and an end cap 14. As can be seen from FIG. 2, the end cap 14 can be removed. The end cap 14 includes a setting tool 16, the purpose of which will be discussed in due course. In a storage configuration shown in FIG. 1, the setting tool 16 is inserted inside a housing body 13 as indicated by the arrow.

Figure 3:
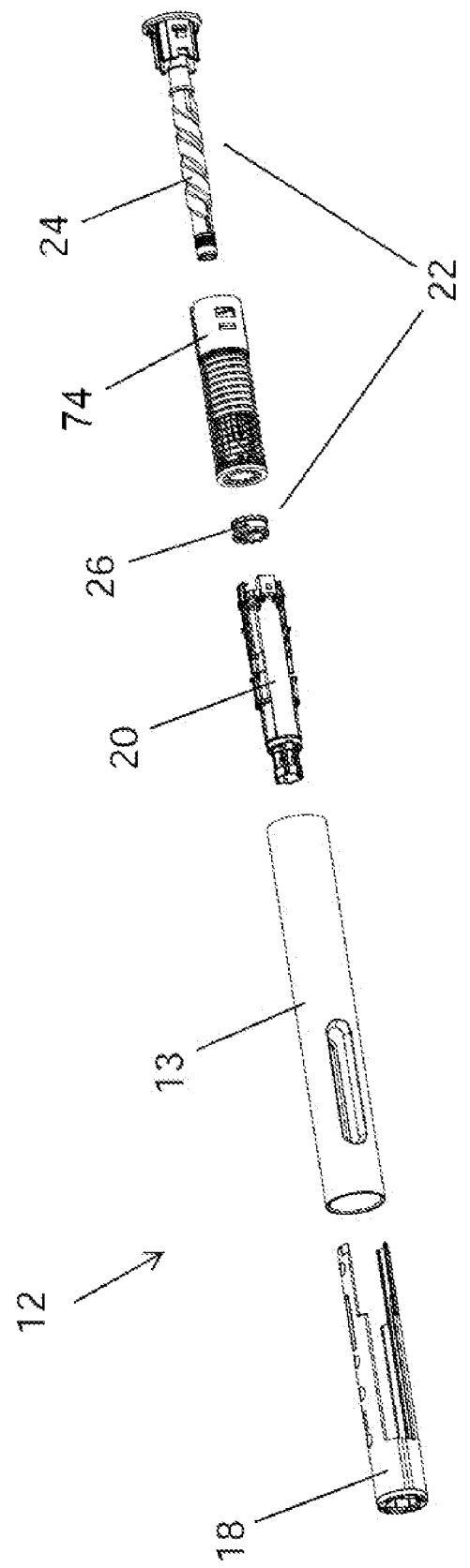
FIG. 3 is an exploded view of the housing assembly of the training device of FIG. 1.

Referring now to FIG. 3, an exploded view of the housing assembly 12 of the training device 10, the housing assembly 12 comprises an initiator 18, a bracket 20, an actuation assembly 22 and a locking mechanism 74.

The actuation assembly 22 comprises a plunger mechanism 24 and a guide member 26, which will now be discussed in more detail with reference to FIG. 4, an assembled view of the actuation assembly 22 and FIG. 5, an exploded view of the actuation assembly 22 of the training device 10.

The plunger mechanism 24 comprises a plunger 30 defining a helical profile 32, a support member 34, a biasing member 36 in the form of a compression spring 38, a rotary damper 40, a retaining clip 42 and an end cap 44.

The helical profile 32 is a double helix, that is, the profile 32 comprises a first helical path 46 and a second helical path 48, the two helical paths 46, 48 being entwined.

Figure 4:
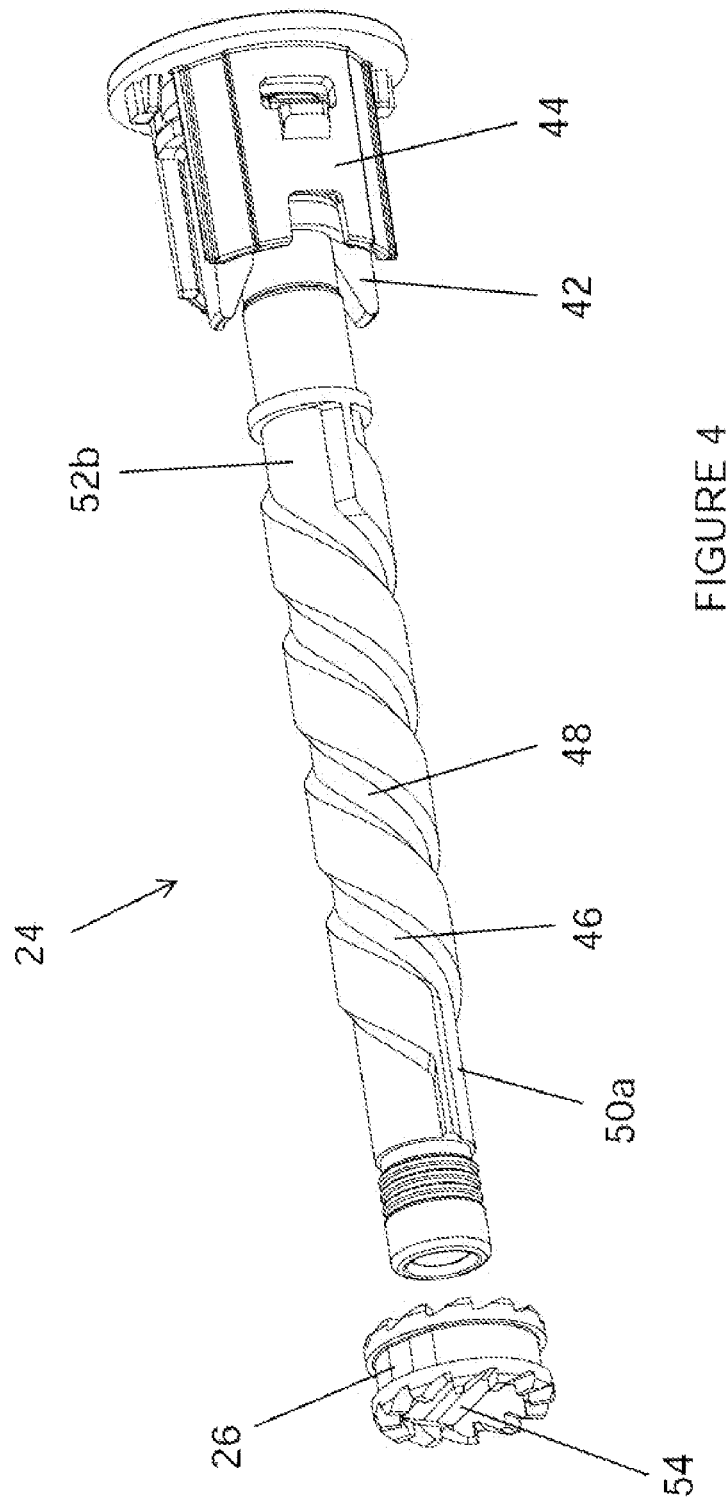
FIG. 4 is an assembled view of the actuation assembly of the training device of FIG. 1.
Figure 5:
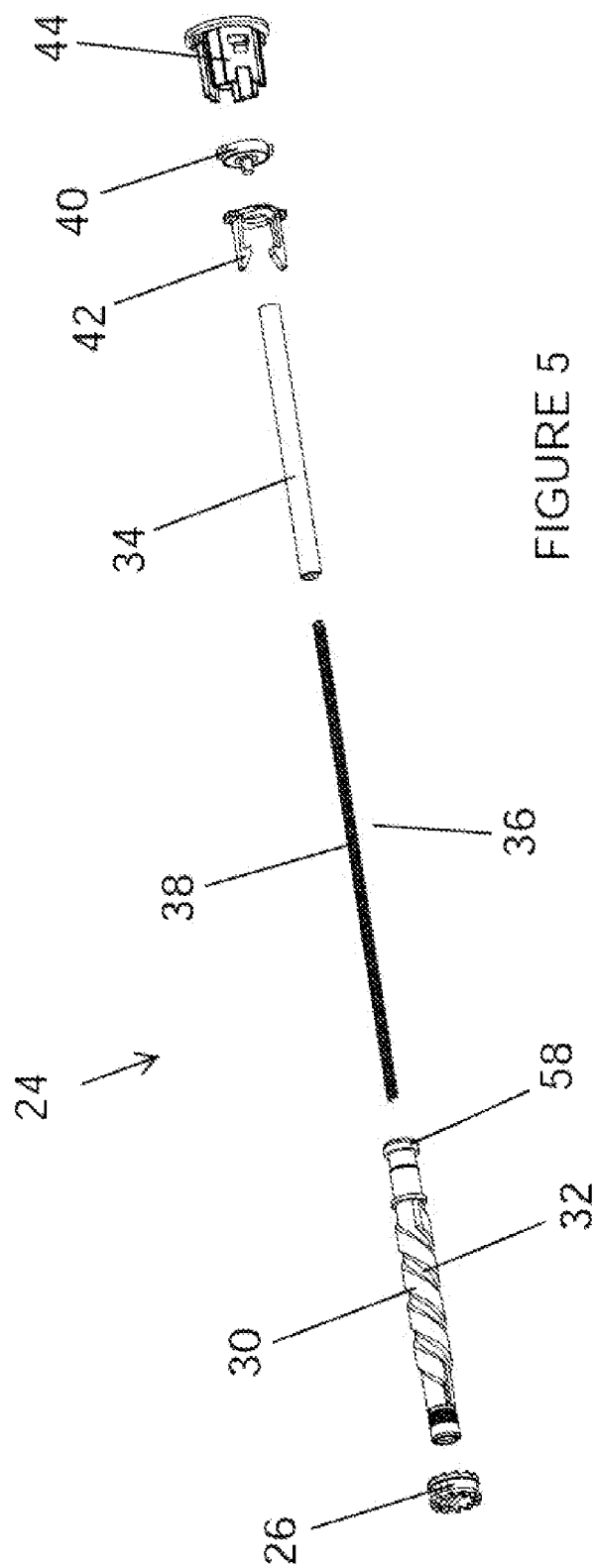
FIG. 5 is an exploded view of the actuation assembly of the training device of FIG. 1.

Both helical paths 46, 48 have a start 50 (only the start 50a of the first helical path 46 is visible on FIG. 4) and a finish 52 (only the finish 52b of the second helical path 48 is visible on FIG. 4).

The guide member 26 has an internal helical profile 54 which is complimentary to the first helical path 46 and the second helical path 48 defined by the plunger 30.

The support member 34 is attached to the rotary damper 40 such that rotation of the support member 34 is damped by the rotary damper 40. The support member 34 is, in turn, telescopically connected to the plunger 30. Furthermore the support member 34 and the plunger 30 are connected by a key and keyway (not shown) relationship, the keyway extending axially along the support member 34. This arrangement permits respective telescopic movement between the support member 34 and the plunger 30, but insurers rotation of one of the plunger 30 and the support member 34 is transmitted to the other of the plunger 30 and support member 34.

The plunger 30 is movable between a start position and a finish position as will be discussed shortly in connection with FIGS. 6 and 7. However, the start position is shown in FIG. 4, and in this position the plunger 30 is retained from moving telescopically with respect to the support member 34 by the retaining clip 42. The retaining clip 42 is engaged with a flange 58 defined by the plunger 30 (FIG. 5). When the retaining clip 42 is opened (as will be discussed in due course) the flange 58 is released from the clip 42, and the plunger 30 can move under the action of the compression spring 38 which is compressed in the start position.

Referring back to FIG. 1, the housing body 13 defines a number of windows 60. These windows 60 allow a view of the interior of the training device 10 and during operation, the plunger 30 moves axially down the housing body 13 past the windows 60 providing a visual indication to the user that the training device 10 is operating correctly and reinforcing the learning of the auto injection method of treatment.

As was described in the background to the invention, one of the challenges of simulating an actual autoinjector is replicating the stroke of the plunger which, in an actual autoinjector is resisted by the liquid medicament being dispensed. This problem is solved in this embodiment of the invention by the combination of the guide member 26 and the rotary damper 40 as will now be described with reference to FIGS. 6 and 7.

Figure 6:
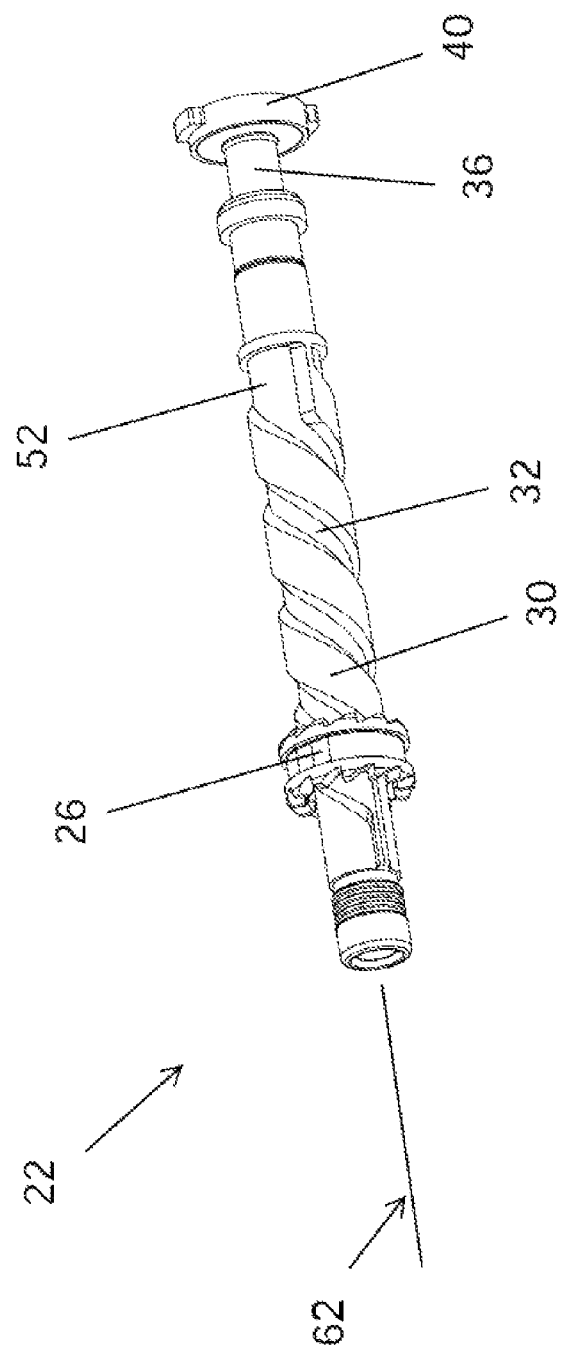
FIG. 6 is a perspective view of part of the actuation assembly of the training device of FIG. 1 in a start position.
Figure 7:
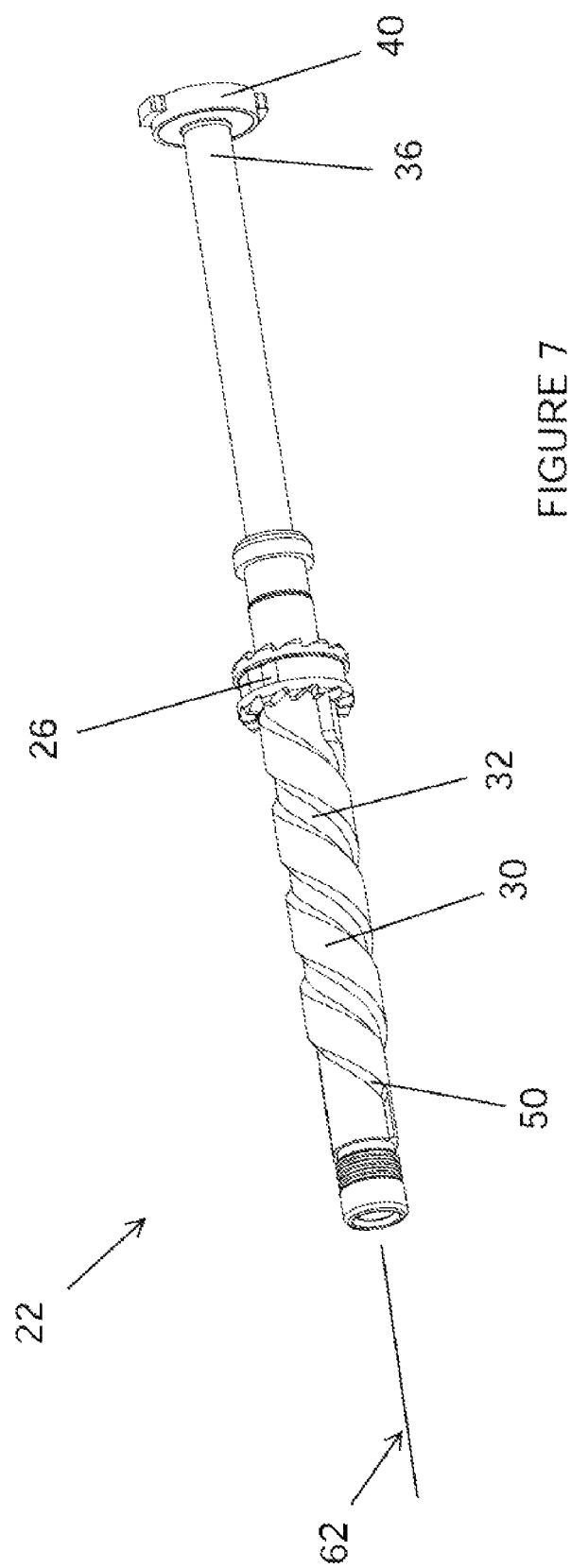
FIG. 7 shows a perspective view of part of the actuation assembly of the training device of FIG. 1 in a finish position.

FIG. 6 shows a perspective view of part of the actuation assembly 22 of the training device 10 in a start position and FIG. 7 shows a perspective view of part of the actuation assembly 22 of the training device 10 in a finish position.

In use, the guide member 26 and the rotary damper 40 are substantially fixed both axially and rotationally with respect to the housing body 13 (not shown). Once the plunger 30 is released by the retaining clip 42 (not shown), the plunger 30 will be urged to move towards the finish position due to the force applied by the compression spring 38 (not shown). As the guide member 26 is substantially fixed rotationally, for the plunger 30 to pass through the guide member 26, the plunger 30 will have to rotate due to the engagement between the helical profile 32 of the plunger 30 and the helical profile 56 (not shown) of the guide member 26. As the plunger 30 moves linearly along a plunger mechanism longitudinal axis 62 between the start position of FIG. 6 and the finish position of FIG. 7, it also takes a rotational path defined by the plunger helical profile 32. As this helical path is non-linear, it increases the length of time the plunger 30 takes to move between the start and finish position (compared to the length of time the plunger 30 would have taken if it had just taken a linear path). Therefore the selection of a particular helical profile 32, or indeed any profile which adds component of movement at an angle to the linear direction of travel, can be used to control and contribute to the speed at which the plunger 30 travels between the start and finish positions.

It will be noted that the start 50 and finish 52 of the helical paths 46, 48 are linear. In use, as the plunger 30 moves from linear to helical travel at the end of the helical path start 50, the engagement between the guide member 26 and the plunger 30 creates an audible click. This replicates the clicking sound of an actual autoinjector when the injection process starts. Similarly as the plunger 30 moves from helical to linear travel at the beginning of the helical path finish 52, a further click is heard, replicating the clicking sound of an actual autoinjector when the injection process finishes.

As the plunger 30 moves from the start position to the finish position, the rotation of the plunger 30 is transmitted to the support member 36 by the key on the plunger 30 engaging with the keyway on the support member 36. This causes rotation of the support member 36. However this rotation is resisted by the rotary damper 40 which rotate in a plane perpendicular to the longitudinal axis 62. This arrangement further dampens the movement of the plunger providing additional force which the helical spring 38 has to overcome to move the plunger 30 along the axis 62 between the start and finish positions.

Figure 8:
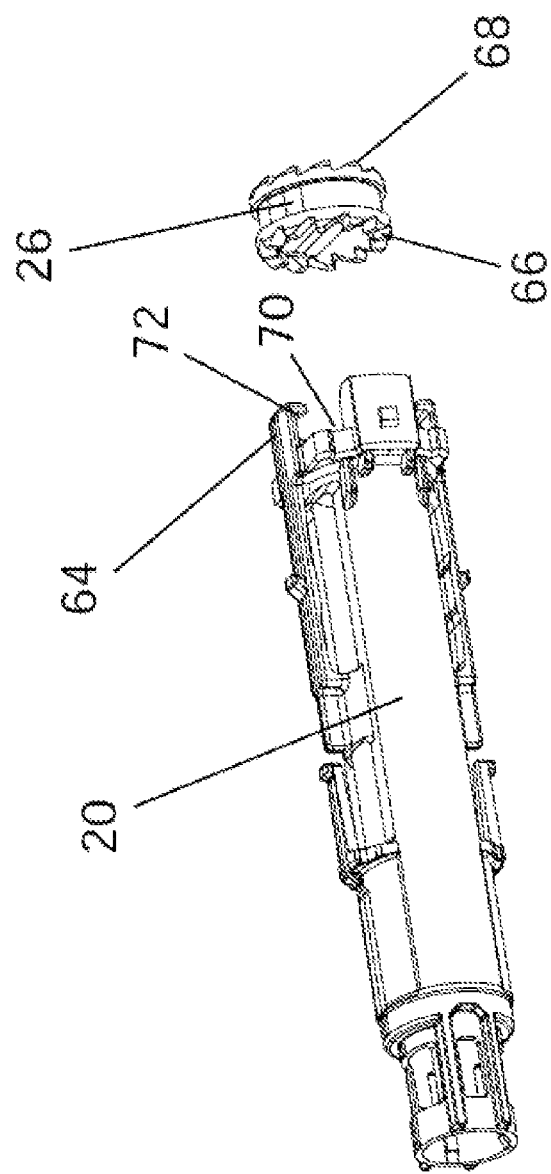
FIG. 8 is a perspective view of the bracket and the guide member of the training device of FIG. 1.

Referring to FIG. 8, a perspective view of the bracket 20 and the guide member 26, the bracket 20 defines a cage 64 in which the guide member 26 sits, the guide member 26 being retained in the cage by a cage lip 72. The cage 64 is sized to allow a small amount of axial movement of the guide member 26, as will be described in due course. The guide member 26 defines a lower serrated edge 66 and an upper serrated edge 68. The serrated edges prevent rotation of the guide member by engagement with a complementary serrated edge on another component.

The bracket cage 64 defines one of the complementary serrated edge 70 which engages the lower serrated edge 66, the action of the plunger 30 pushing the guide member 26 against the complimentary serrated edge 70. The engagement of the serrated edges 66, 70 preventing rotational movement of the guide member 26.

Figure 10:
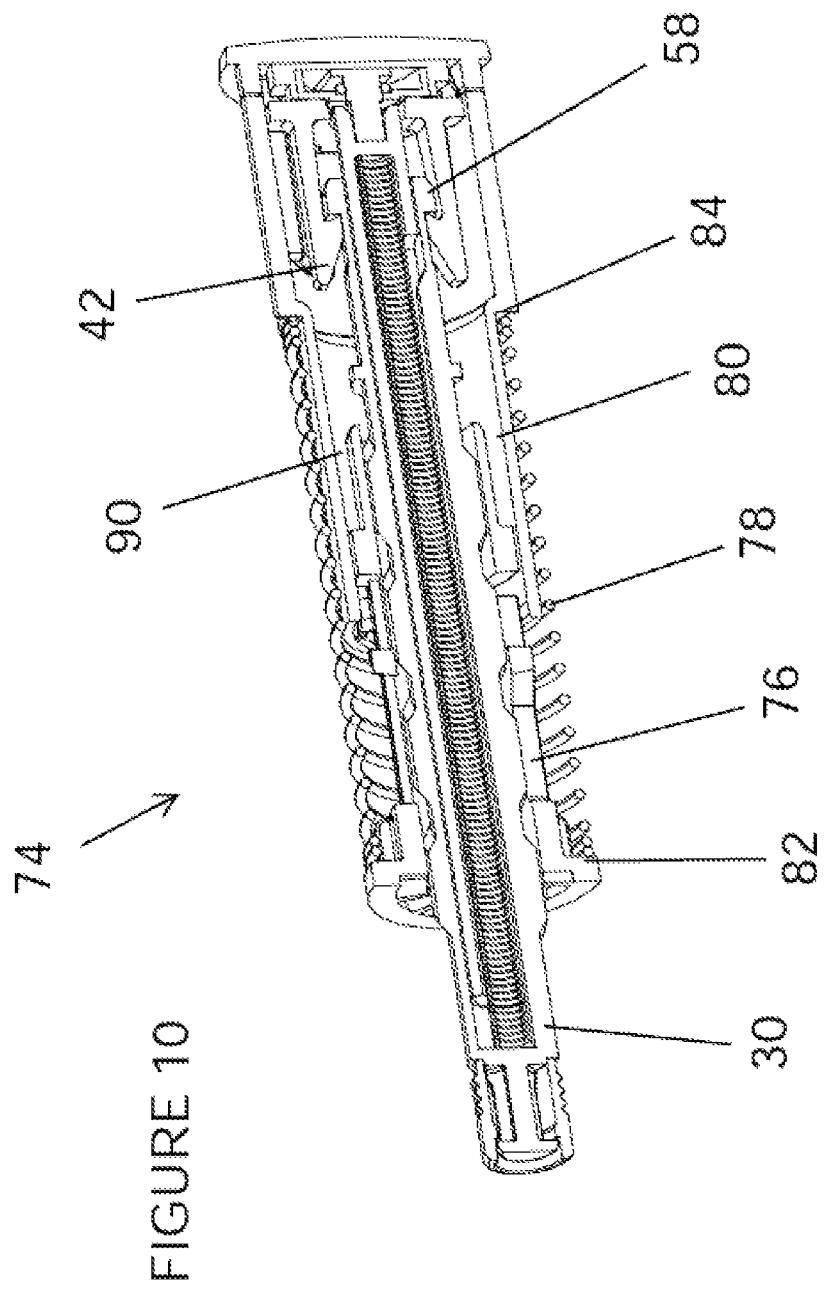
FIG. 10 is a section view through part of the training device of FIG. 1 showing the locking mechanism.

The training device further comprises a locking mechanism 74 which is shown in FIG. 9, a partially exploded perspective view of part of the training device 10 of FIG. 1 showing part of the locking mechanism 74, and FIG. 10 a section view through part of the training device 10 of FIG. 1 showing the locking mechanism 74. The purpose of the locking mechanism is to lock the initiator 18 in the finish position, at least until training device 10 is reset. This is to simulate the real autoinjector which may be for single use. Similarly, in an autoinjector intended for repeated use an interim step is required (e.g. removing the empty medicament container and placing a new one). By locking the training device 10 an interim step of resetting the training device 10 is required making the user experience much more realistic.

The locking mechanism 74 comprises a locking mechanism body 76, a spring 78 and a locking mechanism housing in the form of a collar 80. The spring 78 is located in a recess between a locking mechanism body lip 82 and a collar lip 84, biasing the body 76 and the collar 84 apart.

Also visible on FIG. 9 is the initiator 18. This is the part of the training device 10 which engages the user at the site which medicament is to be injected into. The initiator 18 defines a user engaging surface 86 for this purpose. When a user presses the training device 10 against the skin, the rest of the training device 10 moves towards the use of skin with respect to the initiator 18 which remains stationary. The initiator 18 includes fingers 87 which press against a locking mechanism body surface 88. As the user continues to press the training device 10, further axial movement of the locking mechanism body 76 is prevented and the spring 78 is compressed. Continued application of pressure by the user moves the plunger retaining clip 42 towards a locking mechanism body end 90. Once the retaining clip 42 engages with the locking mechanism body end 90, the retaining clip 42 is forced open releasing the plunger flange 58, thereby allowing the plunger to move from the start position to the finish position.

Figure 11:
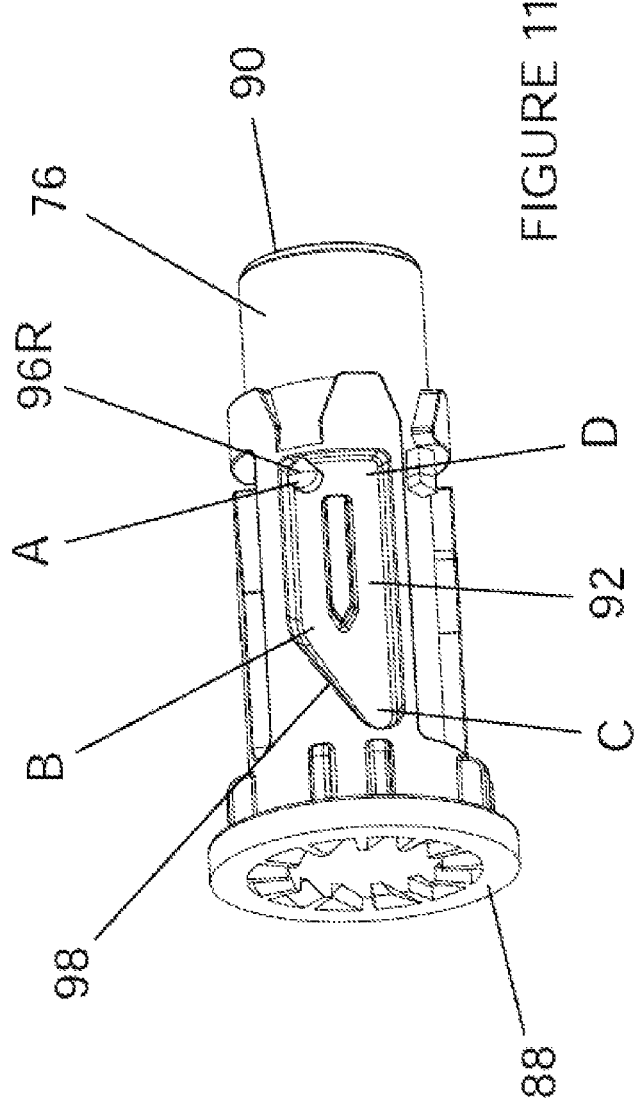
FIG. 11 is a perspective view of the locking mechanism body of the training device of FIG. 1 in a first orientation.
Figure 12:
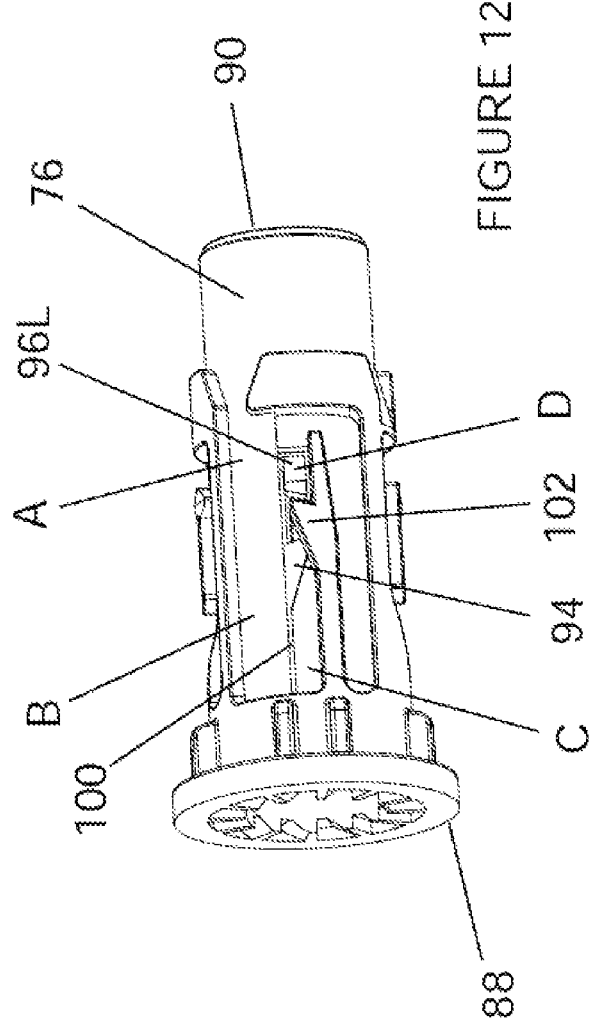
FIG. 12 is a perspective view of the locking mechanism body of the training device of FIG. 1 rotated 35° from the first orientation.

FIG. 11 is a perspective view of the locking mechanism body 76 in a first orientation and FIG. 12 is a perspective view of the locking mechanism body 76 rotated 90° from the first orientation. It can be seen from FIG. 11 that the locking mechanism body defines a rotation track 92. There is another identical rotation track on the opposite side of the locking mechanism body 76.

The locking mechanism body 76 further defines a locking track 94. Again there is an identical locking track on the opposite side of the locking mechanism body 76.

The locking mechanism collar 80 (not shown) defines four blocks 96 which extend from an internal surface of the collar 80 into each of the tracks 92, 94. Two of the blocks 96 are shown, a rotation track block 96R and a locking track block 96L.

When the initiator fingers 87 engage the locking mechanism body surface 88, and the locking mechanism is moved axially towards the retaining clip 42, the blocks 96 travel from point A to point B in their respective tracks 92, 94.

At point B, the rotation blocks 96R engage an angled track surface 98 which causes the locking mechanism body 76 to rotate as the collar 80 is additionally fixed to the training device housing body 13. At point C, the locking mechanism body has reached the extent of its travel and the locking mechanism body end 90 has released the plunger flange 58 from the retaining clips 42. It will be noted that the locking track 94 includes a step 100 which the locking track block 96L goes down in moving from point B to point C.

Upon release of the pressure by the user, the spring 78 will push the locking mechanism body 76 away from the locking mechanism collar 80 and the blocks 96 move from point C to point D in their respective tracks 92, 94.

As shown in FIG. 12, the locking track 94 includes a locking arm 102 which deflects open as the locking track block 96L moves from point C to point D. This locking arm 102 prevents movement back from point D to point C due to a locking arm protrusion 104. Furthermore, the step 100 prevents the locking track block 96L from moving from point D to point A.

In this position the device 10 is locked and will remain unusable until the locking mechanism 28 is released.

Figure 13:
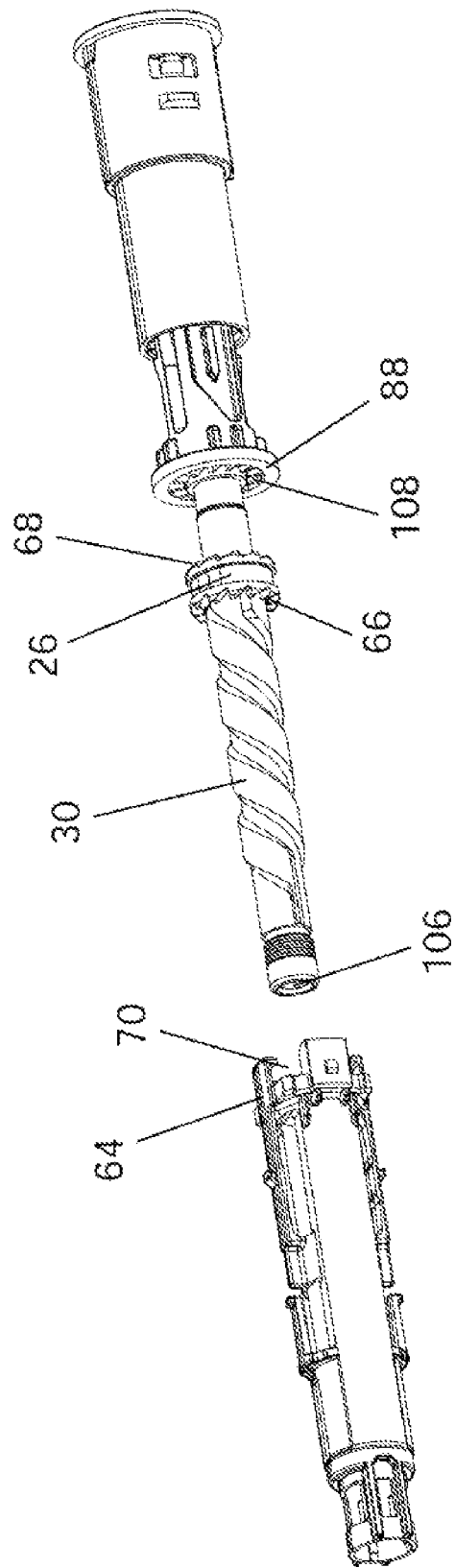
FIG. 13 is a perspective view of part of the training device of FIG. 1 showing the reset procedure.

Reference is now made to FIG. 13, a perspective view of part of the device 10 of FIG. 1 showing the reset procedure. To reset the device 10, the setting tool 16 (FIG. 2) is pushed into the end 106 of the plunger 30. This creates sufficient axial movement of the plunger 30 and the guide member 26 to release the guide member lower serrated edge 66 from the bracket serrated edge 70 and towards the locking mechanism surface 88. The guide member 26 does not leave the bracket cage 64, it just moves slightly axially within the cage 64.

The guide member upper serrated surface 68 then engages a serrated surface 108 defined by the locking mechanism surface 88. The guide member 26 is then rotationally locked and the application of pressure to the plunger creates a rotational force on the guide member sufficient to allow the locking track block 96L to overcome the step 100 and move to the start position point A.

Further application of pressure to the plunger 30 resets the plunger 30 with the plunger flange being pressed into the retaining clip 42. In this position the end cap 14 is back in the position shown in FIG. 1 and the training device 10 is ready for another use.

FIGS. 14 to 22 and 22A show a training device 10 of similar form to that of FIGS. 1 to 13 but with an alternative locking mechanism arrangement.

Figure 14:
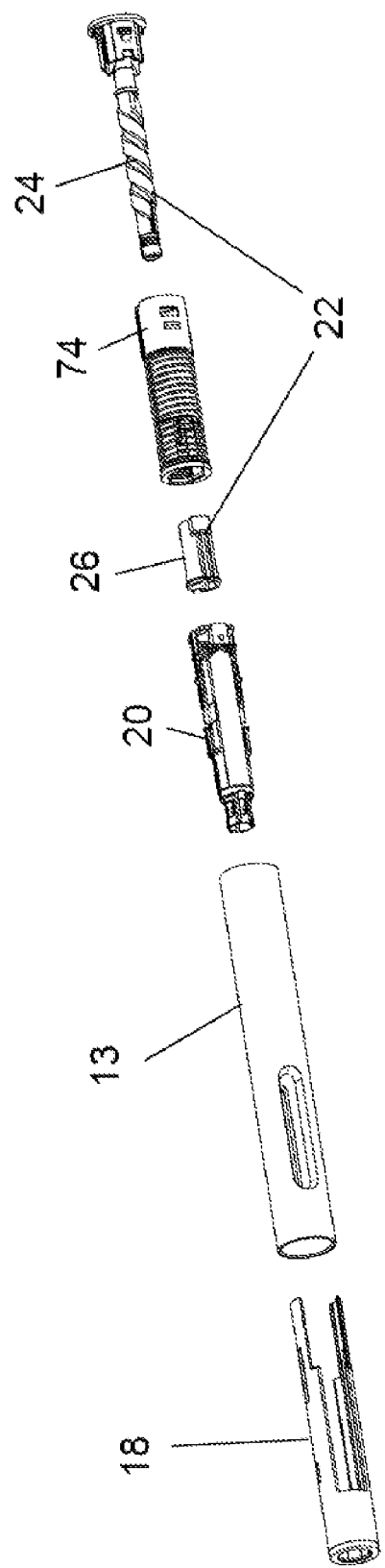
FIG. 14 is a an exploded view of the housing assembly of another training device.

In FIG. 14 an exploded view similar to that of FIG. 3 is shown with like parts numbered the same. The plunger mechanism 24 has generally the same structure as that shown in FIGS. 4 to 7. The guide member 26 of the actuation assembly 22, and the locking mechanism 28, each take a different form as discussed below. When assembled the training device has the same appearance as the embodiment depicted in FIGS. 1 and 2.

Figure 16:
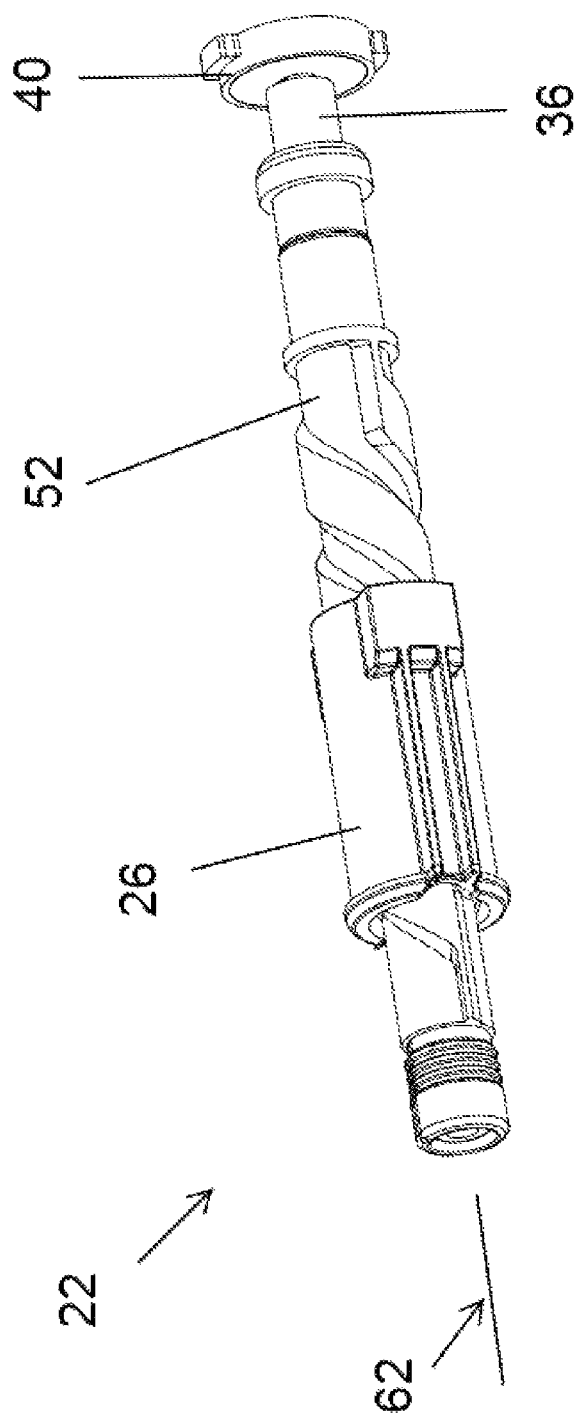
FIG. 16 is a perspective view of the actuation assembly of the training device of FIG. 14.

As shown in more detail in FIGS. 15 and 16 the guide member 26 has an internal helical profile 54 that allows it to fit about and engage with the first and second helical paths 46 and 48 on the plunger 30 in the same way as the apparatus of FIGS. 1 to 13.

Figure 17:
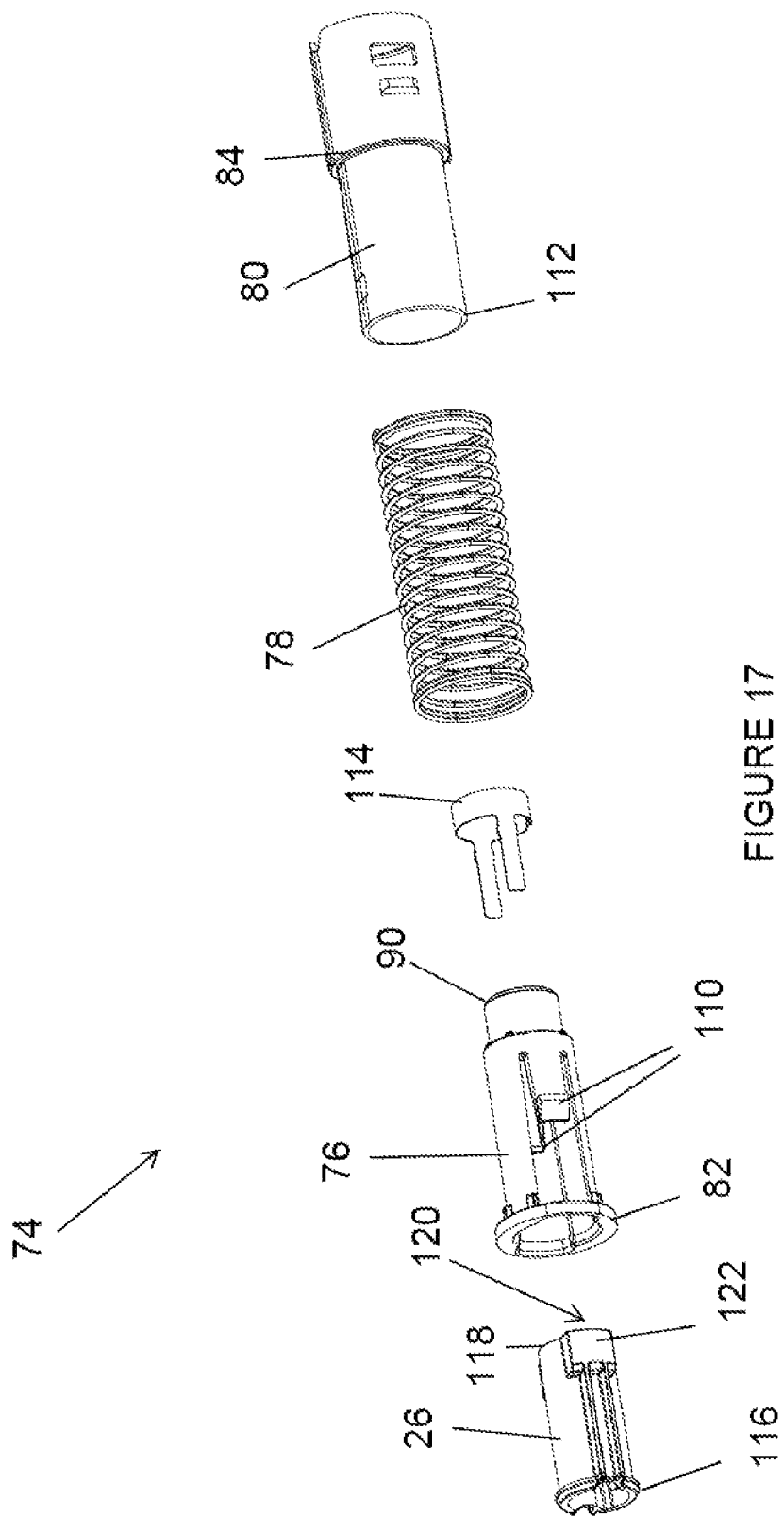
FIG. 17 is an exploded view of the locking mechanism of the training device of FIG. 14.

FIG. 17 shows guide member 26 in relation to an exploded view of locking mechanism 74 (FIG. 15). The locking mechanism 74 comprises a locking mechanism body 76, a spring 78 and a locking mechanism housing in the form of a collar 80. The spring 78 is located in a recess between a locking mechanism body lip 82 and a collar lip 84, biasing the body 76 and the collar 80 apart. When assembled the locking mechanism body 76 and housing (collar 80) are in a telescopic relationship. The locking mechanism body (typically of a plastics material) includes a body end 90 and two resilient projections (clips) 110 which, unless pressed radially inwards, will not pass the end 112 of collar 80 that receives body 76 as it is pushed into it. In this example a metal reinforcing member 114 fits inside projections 110 to provide additional consistency to their action. Guide member 26 includes a distal end 116, and a proximal end 118 including slots 120 in the body of the guide member, in bulges 122 in this example. The slots 120 are for engaging with the locking mechanism body 76. The guide member 26 can slide through the locking mechanism body lip 82 so that slots 120 in bulges 122 can accept projections 110 and drive them radially inwards, sufficient to allow the projections to pass into collar 80.

Figure 18:
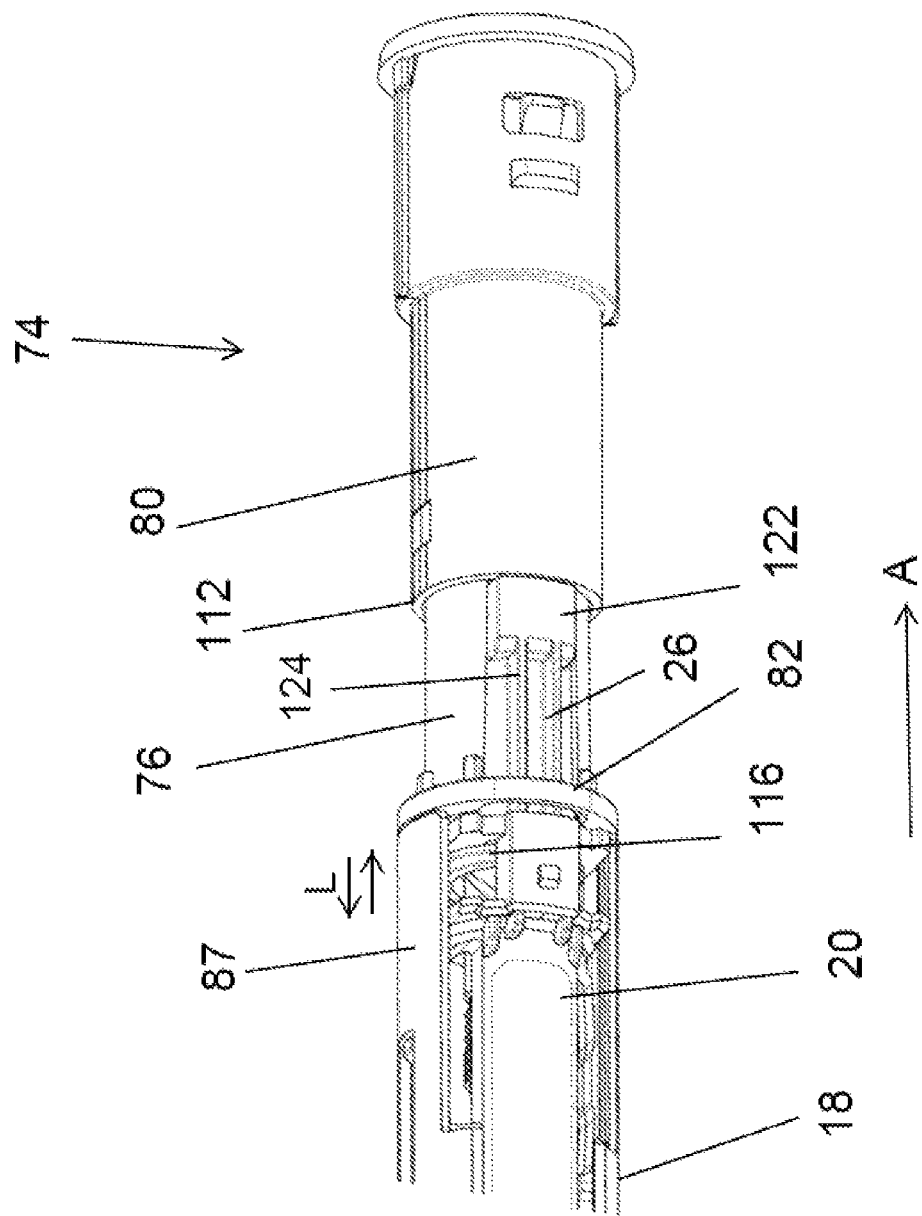
FIG. 18 is a perspective view of the locking mechanism of the training device of FIG. 14.

FIG. 18 shows a partial view of the assembled device including locking mechanism 74 and other internals. Spring 78 (FIG. 17) is not shown for clarity. In FIG. 18 guide member 26 is nested inside locking mechanism body 76 so that projections 110 are accepted into the slots 120 in bulges 122 (neither slots 120 or projections 110 are visible in this view). Guide member 26 is supported by bracket 20 at distal end 116. The guide member is captive but able to have limited linear motion as suggested by arrows L. Guide member 26 is not free to rotate, prevented by ribs 124 which slide in grooves in the bracket. In the position shown the fingers 87 of initiator 18 are contacting lip 82 of the locking mechanism body 76. As a user simulates making an injection by pressing the end of the initiator against their body, the locking mechanism body 76 will move in the direction of arrow A against the resistance of spring 78 (FIG. 17).

Figure 19:
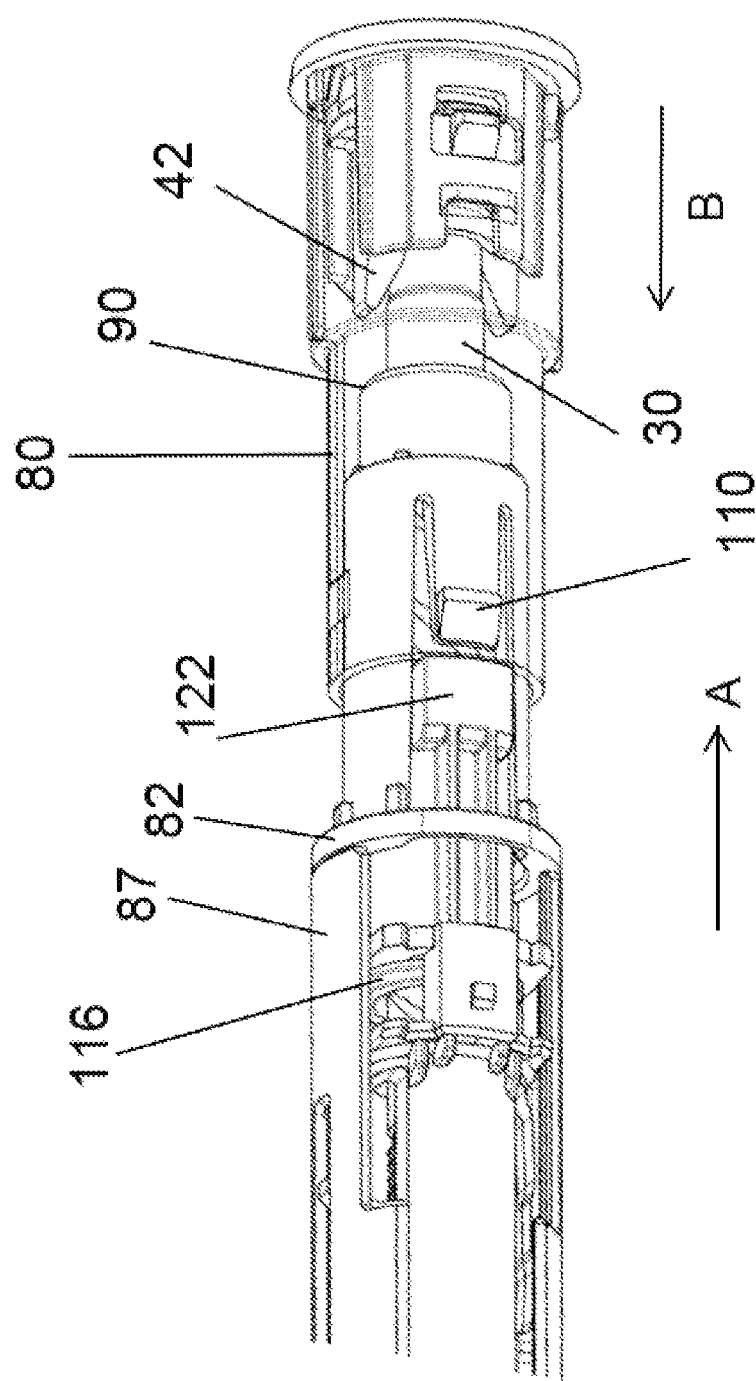
FIG. 19 is a perspective view of the locking mechanism of the training device of FIG. 14.

FIG. 19 shows a similar view to that of FIG. 18 but with the locking mechanism body 76 further advanced in direction A by the action of initiator fingers 87. The locking mechanism collar 80 is transparent in this view to allow viewing inside. In this position projections 110 are sliding inside collar 80 and locking mechanism body end 90 is approaching trigger retaining clip 42 where it will cause release of the plunger 30 to travel in direction B.

Figure 20:
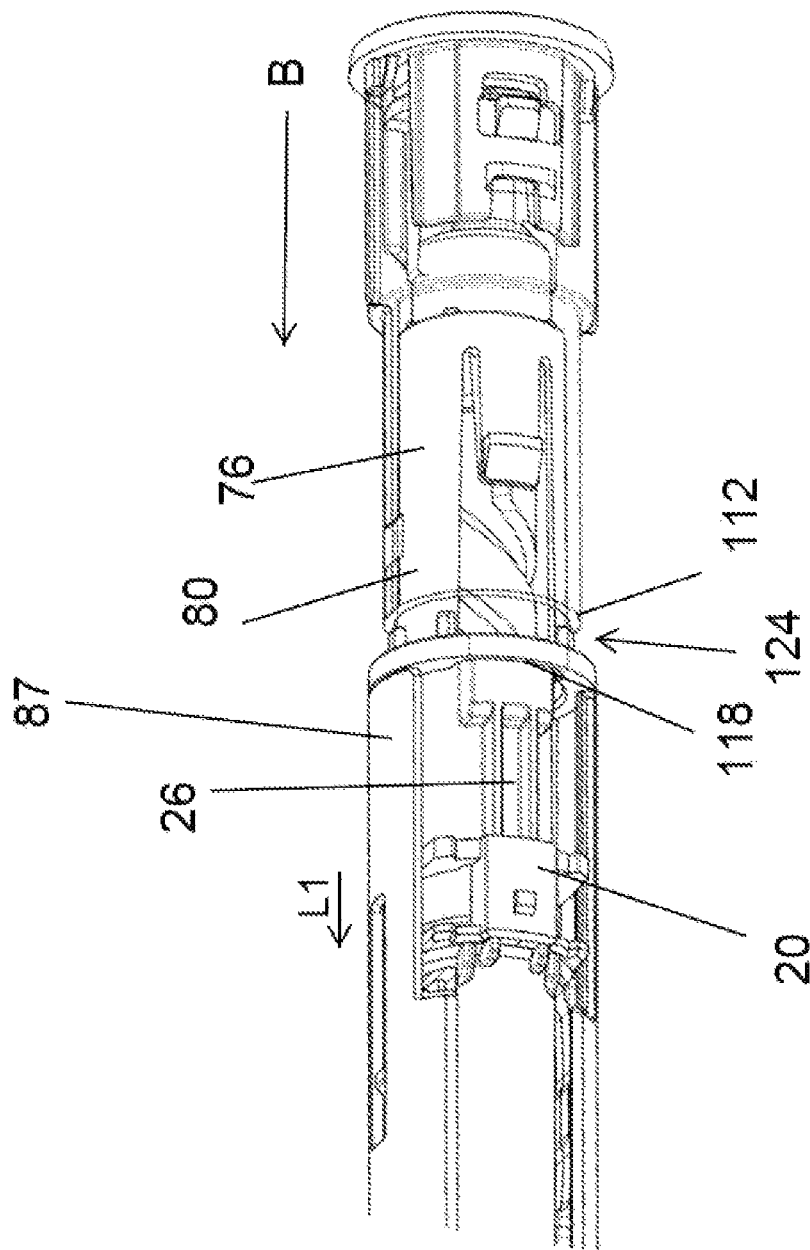
FIG. 20 is a perspective view of the locking mechanism of the training device of FIG. 14.

FIG. 20 shows the situation following release of plunger 30. Movement of plunger 30 in direction B has caused guide member 26 to move in the same direction by the amount allowed by bracket 20 (suggested by arrow L1), This creates a gap 124 between the proximal end 118 of the guide member and the proximal end 112 of the collar 80.

Figure 21:
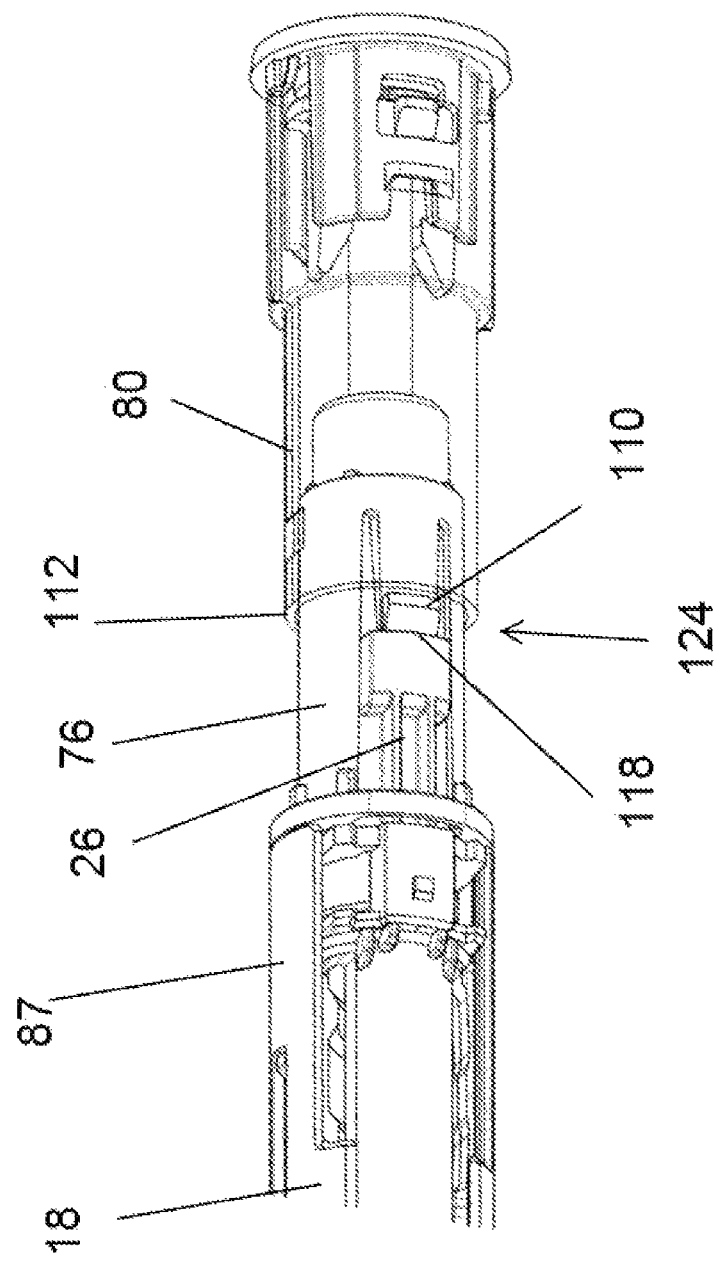
FIG. 21 is a perspective view of the locking mechanism of the training device of FIG. 14.

In FIG. 21 the locking mechanism body 76 has returned to the position with respect to collar 80 it had in FIG. 18, but guide member 26 remains at a spacing of gap 124. This allows the projections 110 to escape radially outwards into gap 124, locking the locking mechanism to the position shown in FIG. 22.

Figure 22:
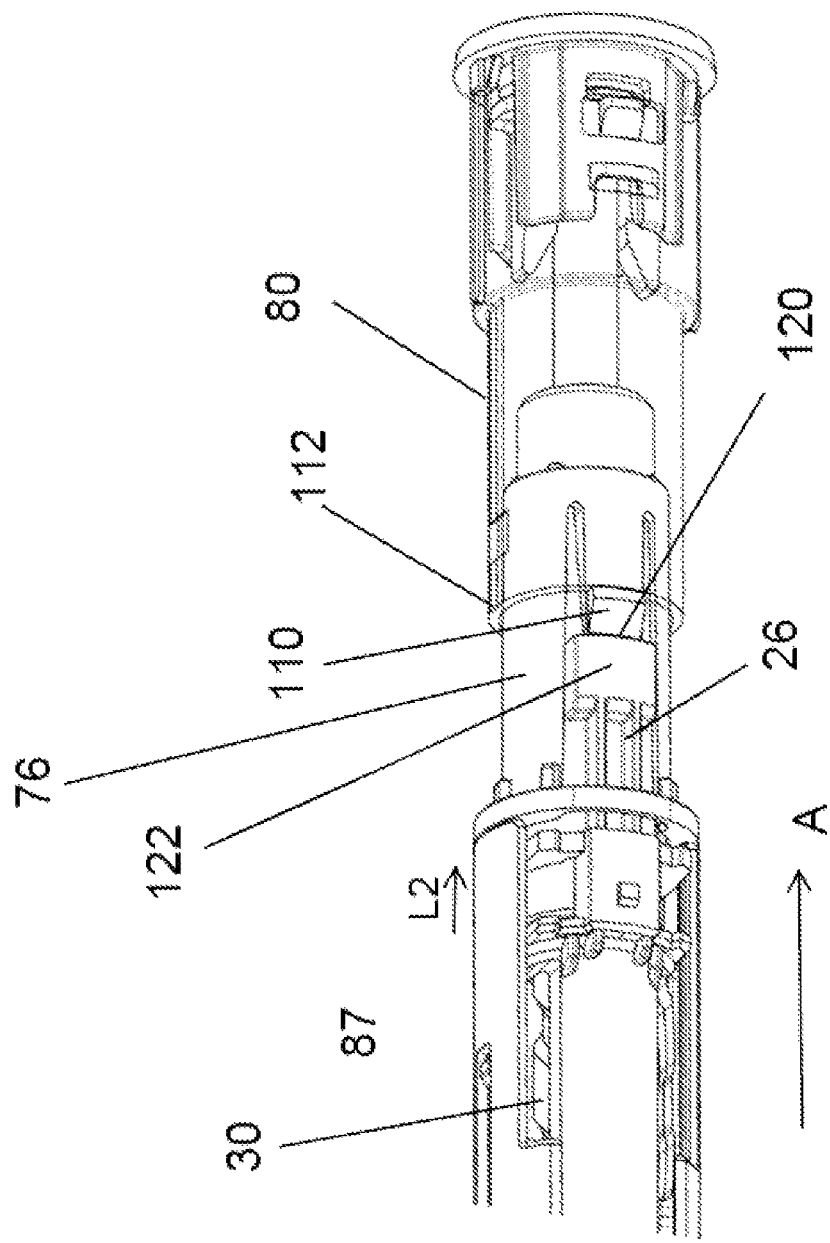
FIG. 22 is a perspective view of the locking mechanism of the training device of FIG. 14.

As shown in FIG. 22 the projections 110 on locking mechanism body 76 prevent travel in direction A, when the body 76 is pushed by initiator fingers 87. The projections 110 but against the proximal end 112 of collar 80. To release the lock, plunger 30 is moved by insertion of setting tool 16 into the device (FIG. 2). This pushes plunger 30 in direction A, in turn moving guide member 26 by the distance L2 (see FIG. 22A, discussed below). Movement L2 allows the slots 120 in bulges 122 of guide member 26 to accept the projections 110 on locking mechanism body 76, deflecting them radially inwards. Thus, the device is returned to the unlocked start position of FIG. 18, where projections 110 can pass into the collar 80.

Figure 22A:
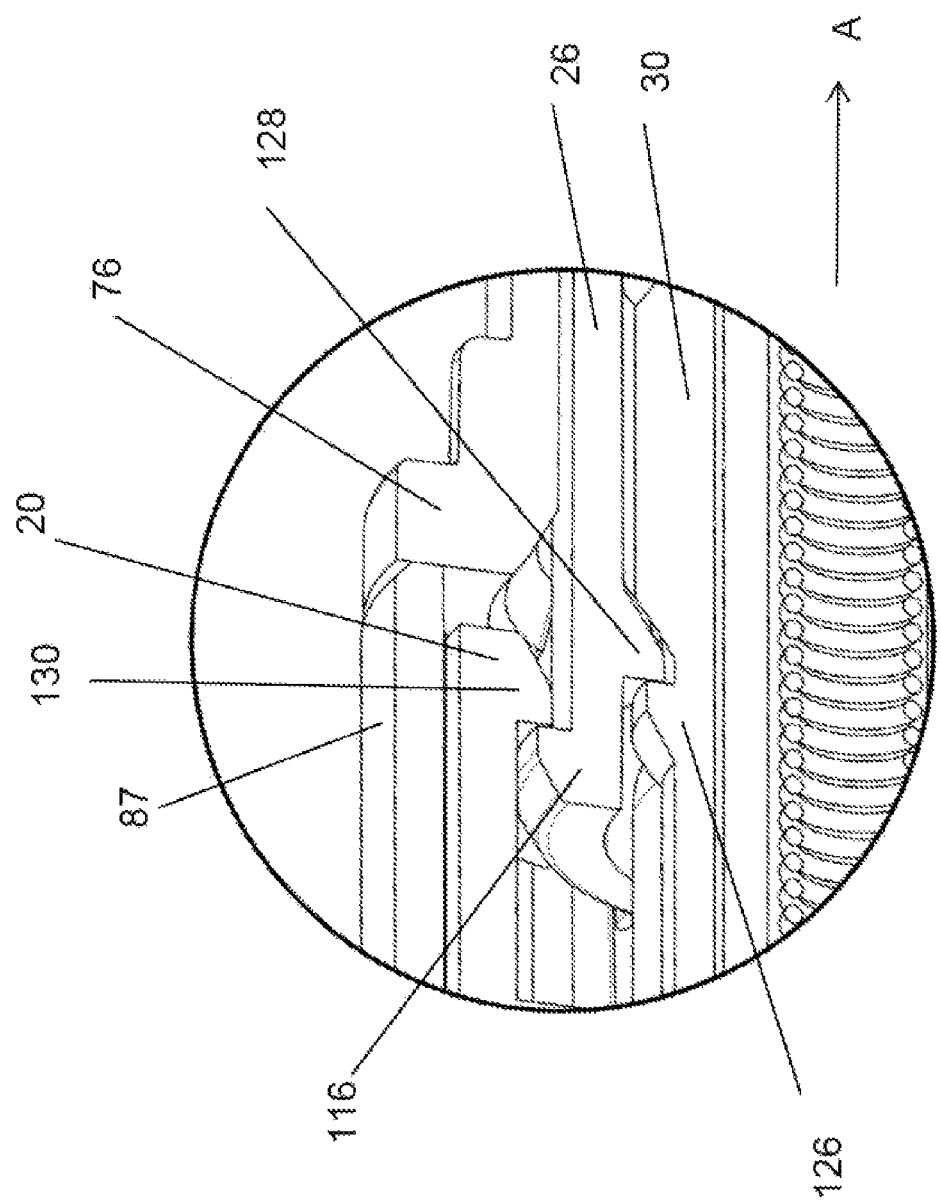
FIG. 22A is a magnified perspective cross section view of part of the locking mechanism of the training device of FIG. 14.

FIG. 22A shows in magnified detail the interaction between the plunger 30 and the guide member 26 in the bracket 20 after the unlocking procedure described above with respect to FIG. 22 has been made. As plunger 30 was moved in the direction A, close to its start position, a projection 126 on the plunger engaged a corresponding projection 128 on the guide member 26, near to its distal end 116. This caused the linear motion L2 indicated by arrow on FIG. 22. The resulting position shown in FIG. 22A has the distal end 116 of guide member 26 abutting the end 130 of bracket 20 i.e. the captive guide member 26 has been moved to the start position shown in FIG. 18.

The invention claimed is:

1. A training device for training a user in the operation of an auto-injector that dispenses a medicament, the training device comprising:
   a housing; and
   a removable cap, the cap cooperating with the housing to provide a sealed unit;
   wherein removal of the cap reveals an open end defined by a cover sleeve, the cover sleeve configured to be the point of engagement with an injection site; and
   wherein the cover sleeve is movable with respect to the housing; and
   an actuation assembly located within the housing, the actuation assembly comprising a plunger and a guide member, the plunger and the guide member defining, and connected by, a complementary first male profile and a first female profile, the plunger being movable with respect to the guide member along a first path defined by at least a portion of the first male or the first female profiles, the plunger moving linearly between a start position and a finish position,
   wherein the first path extends in a direction non-parallel to the linear movement of the plunger,
   wherein the actuation assembly further comprises a rotary damper, and
   wherein the training device comprises a locking mechanism configured to prevent further operation of the device until the device is unlocked.

2. The training device of claim 1, wherein the guide member defines a throughbore, the plunger passing through the throughbore.

3. The training device of claim 1, wherein the plunger defines a bore, the guide member being connected to an internal surface of the plunger.

4. The training device of claim 1, wherein the first path is serpentine.

5. The training device of claim 1, wherein the actuation assembly further comprises a biasing mechanism.

6. The training device of claim 5, wherein the biasing mechanism is an energy accumulating member.

7. The training device of claim 1, wherein the actuation assembly further comprises a support member configured to support the plunger as it moves between the start position and the finish position.

8. The training device of claim 7, wherein the support member is axially fixed with respect to the plunger.

9. The training device of claim 7, wherein the support member is rotationally connected to the plunger.

10. The training device of claim 7, wherein the support member is connected to the rotary damper such that rotation of the support member is damped by the rotary damper.

11. The training device of claim 7, wherein the plunger is in a sliding relationship with the support member.

12. The training device of claim 7, wherein the plunger is in a sliding relationship with the support member.

13. The training device of claim 1, wherein the training device comprises a trigger mechanism to trigger the actuation mechanism to start the movement of the plunger from the start position.

14. The training device of claim 13, wherein the trigger mechanism triggers the actuation mechanism upon a user pressing the training device against a surface.

15. The training device of claim 1, wherein the training device comprises a release mechanism configured to unlock the locking mechanism and reset the training device.

16. The training device of claim 15, wherein the release mechanism is configured to engage the guide member with the locking mechanism, engagement of the guide member with the locking mechanism releasing the locking mechanism.

17. The training device of claim 1, wherein the training device includes at least one sensor adapted to provide feedback to user on the successful operation of the device.

18. The training device of claim 1, wherein the first path encircles the plunger longitudinal axis and is helical.

19. The training device of claim 1, wherein there are two paths, the first path and a second path, that define a double helix.

20. A training device for training a user in the operation of an auto-injector that dispenses a medicament, the training device comprising:
- a housing; and
- an actuation assembly located within the housing, the actuation assembly comprising a plunger and a guide member, the plunger and the guide member defining, and connected by, a complementary first male profile and a first female profile, the plunger being movable with respect to the guide member along a first path defined by at least a portion of the first male or the first female profiles, the plunger moving linearly between a start position and a finish position,
- wherein the first path extends in a direction non-parallel to the linear movement of the plunger,
- wherein the actuation assembly further comprises a rotary damper;
- wherein the training device comprises a locking mechanism configured to prevent further operation of the device until the device is unlocked;
- wherein the training device comprises a removable cap, the cap cooperating with the housing to provide a sealed unit;
- wherein the training device comprises a release mechanism configured to unlock the locking mechanism and reset the training device; and
- wherein the release mechanism is part of the removable cap.

21. A training device for training a user in the operation of an auto-injector that dispenses a medicament, the training device comprising:
- a housing; and
- an actuation assembly located within the housing, the actuation assembly comprising a plunger and a guide member, the plunger and the guide member defining, and connected by, a complementary first male profile and a first female profile, the plunger being movable with respect to the guide member along a first path defined by at least a portion of the first male or the first female profiles, the plunger moving linearly between a start position and a finish position,
- wherein the first path extends in a direction non-parallel to the linear movement of the plunger,
- wherein the actuation assembly further comprises a rotary damper;
- wherein the training device comprises a locking mechanism configured to prevent further operation of the device until the device is unlocked;
- wherein the training device comprises a removable cap, the cap cooperating with the housing to provide a sealed unit;
- wherein the training device comprises a release mechanism configured to unlock the locking mechanism and reset the training device; and
- wherein replacement of the removable cap releases the locking mechanism.

* * * * *